(12) United States Patent
Katsu et al.

(10) Patent No.: US 7,776,885 B2
(45) Date of Patent: *Aug. 17, 2010

(54) BENZIMIDAZOLONE COMPOUNDS HAVING 5-HT4 RECEPTOR AGONISTIC ACTIVITY

(75) Inventors: Yasuhiro Katsu, Chita-gun (JP); Satoru Iguchi, Chita-gun (JP); Hiroki Sone, Chita-gun (JP); Chikara Uchida, Chita-gun (JP); Takashi Kojima, Chita-gun (JP)

(73) Assignee: Pfizer, Inc., New York, NY (US)

( * ) Notice: Subject to any disclaimer, the term of this patent is extended or adjusted under 35 U.S.C. 154(b) by 827 days.

This patent is subject to a terminal disclaimer.

(21) Appl. No.: 10/933,629

(22) Filed: Sep. 2, 2004

(65) Prior Publication Data

US 2005/0148573 A1 Jul. 7, 2005

Related U.S. Application Data

(60) Provisional application No. 60/500,144, filed on Sep. 3, 2003.

(51) Int. Cl.
*A61K 31/454* (2006.01)
*C07D 471/04* (2006.01)

(52) U.S. Cl. .......... 514/322; 514/210.16; 514/304; 514/394; 546/121; 546/124; 546/199

(58) Field of Classification Search ........... 514/210.16, 514/304, 322, 394; 546/121, 124, 199
See application file for complete search history.

(56) References Cited

U.S. PATENT DOCUMENTS

| 5,223,511 | A | 6/1993 | Turconi et al. ............ 514/304 |
| 5,705,498 | A | 1/1998 | Gaster et al. ............. 514/214 |
| 6,106,864 | A | 8/2000 | Dolan et al. ............. 424/488 |
| 6,207,697 | B1 | 3/2001 | Han et al. ............... 514/409 |
| 6,420,410 | B1 | 7/2002 | Sperl et al. ............. 514/395 |
| 6,552,042 | B2 | 4/2003 | Han et al. ............... 514/322 |
| 2005/0277671 | A1 | 12/2005 | Ando et al. |
| 2005/0277672 | A1 | 12/2005 | Ando et al. |
| 2005/0277673 | A1 | 12/2005 | Ando et al. |
| 2006/0270652 | A1* | 11/2006 | McKinnell et al. ..... 514/210.02 |

FOREIGN PATENT DOCUMENTS

| WO | WO 9111172 | 8/1991 |
| WO | WO 9318027 | 9/1993 |
| WO | WO 9400449 | 1/1994 |
| WO | WO 9402518 | 2/1994 |
| WO | WO 9410174 | 5/1994 |
| WO | WO 9855148 | 12/1998 |
| WO | WO 9912903 | 3/1999 |
| WO | WO 9917772 | 4/1999 |
| WO | WO 0035298 | 6/2000 |

OTHER PUBLICATIONS

Uchida et al. "A preparation of 1-isopropyl . . . " CA 143:193913 (2005).*
Hedge "5Ht4 receptors in gastrointestinal tract" CA 130:61143 (1998).*
Sanger et al. "Therapeutic application . . . " CA 130:61145 (1998).*
Ando et al. "Preparation of benzimidazo . . . " Ca 144:36344 (2005).*
Silverman "The organic chemistr . . . " p. 73 (1993).*
Lopez-Rodriguez et al. "5NT4 receptor antagonist . . . " Current topic in med. chem. vol. 2, p. 625-641 (2002).*
Ueki, S., et al., "Gastroprokinetic Activity of Nizatidine during the Digestive State in the Dog and Rat", *Arzneim.-Forsch./Drug Res.*, 49(II), pp. 618-625 (1999).
Bertram, G. et al., "Total Synthesis of (±)-Strobilurin E", *Tetrahedron Letters*, vol. 37, No. 44, pp. 7955-7958 (1996).
Mattalia, G., et al., "Synthesis of New Derivatives of the 4.5-Diphenytoxazole Series", *Il Farmaco—Ed. Sc.*, vol. 31, pp. 457-467 (1975).
Hazra, B., et al., "An Improved Procedure for the Dichloroacetylation of Primary and Secondary Amines", *OPPI Briefs*, vol. 21, No. 3, pp. 355-358 (1989).
Reeves, J.J., et al., "Investigation into the 5-hydroxytryptamine receptor mediating smooth muscle relaxation in the rat oesophagus", *Br. J. Pharmacol.*, vol. 103, pp. 1067-1072 (1991).

(Continued)

*Primary Examiner*—Celia Chang
(74) *Attorney, Agent, or Firm*—Jennifer A. Kispert; Martha G. Munchhof

(57) ABSTRACT

This invention provides a compound of the formula (I):

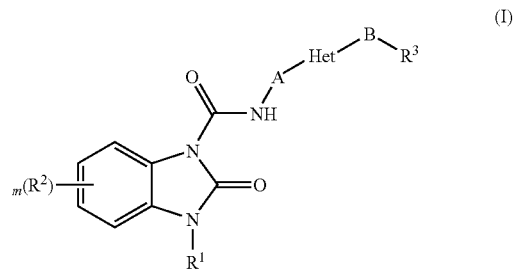

or a pharmaceutically acceptable salt thereof, and compositions containing such compounds and the use of such compounds for the manufacture of medicament for gastroesophageal reflux disease, gastrointestinal disease, gastric motility disorder, non-ulcer dyspepsia, functional dyspepsia, irritable bowel syndrome (IBS), constipation, dyspepsia, esophagitis, gastroesophageral disease, nausea, central nervous system disease, Alzheimer's disease, cognitive disorder, emesis, migraine, neurological disease, pain, cardiovascular disorders, cardiac failure, heart arrhythmia, diabetes and apnea syndrome.

These compounds have 5-HT$_4$ receptor agonistic activity, and thus are useful for the treatment of gastroesophageal reflux disease, non-ulcer dyspepsia, functional dyspepsia, irritable bowel syndrome or the like in mammalian, especially humans.

12 Claims, No Drawings

OTHER PUBLICATIONS

Baxter, G.S., et al., "5-Hydroxytriptamine$_4$ receptors mediate relaxation of the rate oesophageal tunica muscularis mucosae", *Naunyn-Schmiedeberg's Arch. Phamacol.*, vol. 343, pp. 439-446 (1991).

Kaumann, A., et al., "A 5-HT$_4$-like receptor in human right atrium", *Naunyn-Schmiedeberg's Arch. Phamacol.*, vol. 344, pp. 150-159 (1991).

Bockaert, J.; et al., "5-HT$_4$ Receptors Potential Therapeutic Implications in Neurology and Psychiatry", *CNS Drugs*, vol. 1(1), pp. 6-15 (1994).

Romanelli, M.N., et al., "Synthesis and Biological Activity of a Series of Aryl Tropanyl Esters and Amides Chemically Related to 1H-Indole-3-carboxylic Acid endo 8-Methyl-8-azabicyclo[3.2.1]oct-3-yl Ester", *Arzneim.-Forsch./Drug. Res.* vol. 43(II), Nr. 8, pp. 913-918 (1993).

Gullikson, G., et al., "Gastrointestinal Motility Responses to the S and R Enantiomers of Zacopride, a 5-HT4 Agonist and 5-HT3 Antagonist", *Drug Development Research*, vol. 26, pp. 405-417 (1992).

Ford, A., et al., "The 5-HT$_4$ Receptor", *Medicinal Research Reviews*, vol. 13, No. 6, pp. 633-662 (1993).

Prugh, J., et al., "A Simple Method of Protecting a Secondary Amine with tert Butyloxycarbonyl (BOC) in the Presence of a Primary Amine", *Synthetic Communications*, vol. 22(16), pp. 2357-2360 (1992).

Tapia, I., et al., "2,3-Dihydro-2-oxo-1*H*-benzimidazole-1-carboxamides with Selective Affinity for the 5-HT$_4$ Receptor: synthesis and Structure—Affinity and Structure—Activity Relationships of a New Series of Partial Agonist and Antagonist Derivatives", *J. Med. Chem.*, vol. 42, pp. 2870-2880 (1999).

Okamura, W., et al., "Thermal [1,7]-Sigmatropic Shift of Previtamin D$_3$ to Vitamin D$_3$: Synthesis and Study of Pentadeuterio Derivatives", *J. Org. Chem.*, vol. 58, pp. 600-610 (1993).

Bose, D., et al., "Boron Trifluoride Promoted Cleavage of Benzyl Carbamates", *Tetrahedron Letters*, vol. 31, No. 47, pp. 6903-6906 (1990).

Mine, Y., "Comparison of Effect of Mosapride Citrate and Existing 5-HT$_4$ Receptor Agonists on Gastro Intestinal Motility In Vivo and In Vitro", *The Journal of Pharmacology and Experimental Therapeutics (JPET)*, vol. 283, No. 3, pp. 1000-1008 (1997).

Finnin, B., et al., "Transdermal Penetration Enhancers: Applications, Limitations, and Potential", *Journal of Pharmaceutical Sciences*, vol. 88, No. 10, pp. 955-958 (1999); Published on Web Sep. 15, 1999.

Liang, A., et al., "Fast-dissolving intraoral drug delivery systems", *Expert Opin. Ther. Patents*, vol. 11(6), pp. 981-986 (2001).

Finlayson, K. et al., "[$^3$H]Dofetilide binding to HERG transfected membranes: a potential high throughput preclinical screen", *European Journal of Pharmacology*, vol. 430, pp. 147-148 (2001).

Cavero, I., et al., "Drugs that prolong QT interval as an unwanted effect: assessing their likelihood of inducing hazardous cardiac dysrhythmias", *Exp. Opin. Pharmacother.*, vol. 1(5), pp. 947-973 (2000).

Eglen, R., "Central 5-HT$_4$ Receptors", *TIPS Reviews*, vol. 16, pp. 391-398 (1995).

Bockaert, J., "The 5-HT$_4$ receptor: a place in the sun", *TIPS Reviews*, vol. 13, pp. 141-145 (1992).

Thornton, T., et al., "Quinazoline Antifolate Thymidylate Synthase Inhibitors: Difluoro-Substituted Benzene Ring Analogues", *J. Med. Chem.*, vol. 35, pp. 2321-2327 (1992).

Berge, S., et al., "Pharmaceutical Salts", *Journal of Pharmaceutical Sciences*, vol. 66, No. 1, pp. 1-19 (1977).

Verma, et al., "Current Status of Drug Delivery Technologies and Future Directions", *Pharmaceutical Technology On-Line*, vol. 25(2), pp. 1-14 (2001).

Droppleman, D., et al., "A Simplified Method for Assessing Drug Effects on Gastric Emptying in Rats" *J. Pharmacol. Methods*, vol. 4, pp. 227-230 (1980).

Satyamurthy, N., et al., "Synthesis and Stereochemistry of 1-oxa-6-heteraspiro[2.5]octanes. Single-crystal analysis of 6-phenyl-1-oxa-6-phosphaspiro[2.5]octane 6-sulfide", *Phosphorus and Sulfur*, vol. 19, pp. 113-129 (1984).

Schelsinger, et al., "N-Substituted-amides", *J. Amer. Chem. Soc.*, vol. 78, pp. 6123-6127 (1956).

\* cited by examiner

BENZIMIDAZOLONE COMPOUNDS HAVING 5-HT4 RECEPTOR AGONISTIC ACTIVITY

This application claims benefit of priority under 35 U.S.C. §119(e) to U.S. Provisional Application No. 60/500,144, filed Sep. 3, 2003, which is incorporated herein in its entirety by reference.

TECHNICAL FIELD

This invention relates to novel benzimidazolone compounds. These compounds have selective 5-HT$_4$ receptor agonistic activity. The present invention also relates to a pharmaceutical composition, a method of treatment and use comprising the above compounds for the treatment of disease conditions mediated by 5-HT$_4$ receptor activity.

BACKGROUND ART

In general, 5-HT$_4$ receptor agonists are found to be useful for the treatment of a variety of diseases such as gastroesophageal reflux disease, gastrointestinal disease, gastric motility disorder, non-ulcer dyspepsia, functional dyspepsia, irritable bowel syndrome (IBS), constipation, dyspepsia, esophagitis, gastroesophageral disease, nausea, central nervous system disease, Alzheimer's disease, cognitive disorder, emesis, migraine, neurological disease, pain, cardiovascular disorders, cardiac failure, heart arrhythmia, diabetes and apnea syndrome (See *TiPs*, 1992, 13, 141; Ford A. P. D. W. et al., *Med. Res. Rev.*, 1993, 13, 633; Gullikson G. W. et al., *Drug Dev. Res.*, 1992, 26, 405; Richard M. Eglen et al, *TiPS*, 1995, 16, 391; Bockaert J. Et al., *CNS Drugs*, 1, 6; Romanelli M. N. et al., *Arzheim Forsch./Drug Res.*, 1993, 43, 913; Kaumann A. et al., *Naunyn-Schmiedeberg's*. 1991, 344, 150; and Romanelli M. N. et al., *Arzheim Forsch./Drug Res.*, 1993, 43, 913). Also, Mosapride is known to be useful for the treatment of diabetes.

It would be desirable if there were provided 5-HT$_4$ receptor agonists which have more 5HT$_4$ receptor agonistic activities.

U.S. Pat. No. 5,223,511 discloses benzimidazole compounds as 5-HT$_4$ receptor antagonists. Especially, compounds represented by the following formula is disclosed:

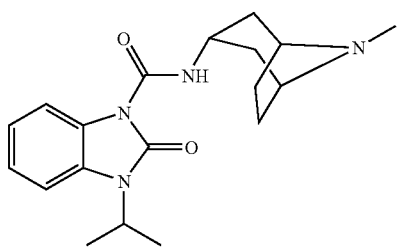

Compound A

WO93/18027 discloses benzimidazolone compounds as 5-HT$_4$ receptor antagonists. Especially, compounds represented by the following formula is disclosed:

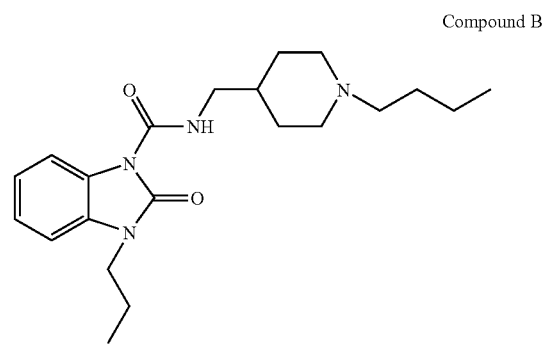

Compound B

WO99/17772 discloses benzimidazolone compounds as 5-HT$_4$ receptor agonists and/or antagonists. Especially, compounds represented by the following formula is disclosed:

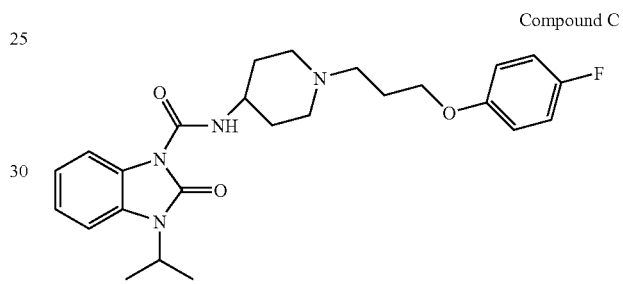

Compound C

WO94/00449 discloses benzimidazolone compounds as 5-HT$_4$ agonists or antagonists and/or 5-HT$_3$ antagonists. Especially, compounds represented by the following formula is disclosed:

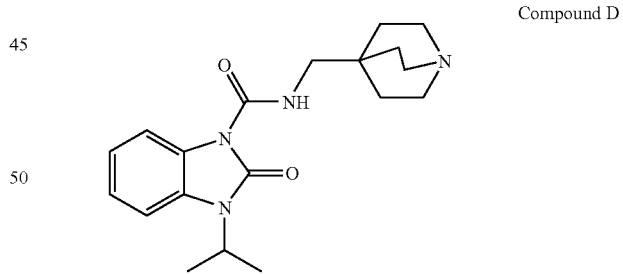

Compound D

There is a need to provide new 5-HT$_4$ agonists that are good drug candidates. In particular, preferred compounds should bind potently to the 5-HT$_4$ receptor whilst showing little affinity for other receptors and show functional activity as agonists. They should be well absorbed from the gastrointestinal tract, be metabolically stable and possess favorable pharmacokinetic properties. When targeted against receptors in the central nervous system they should cross the blood brain barrier freely and when targeted selectively against receptors in the peripheral nervous system they should not cross the blood brain barrier. They should be non-toxic and demonstrate few side-effects. Furthermore, the ideal drug candidate will exist in a physical form that is stable, non-hygroscopic and easily formulated.

BRIEF DISCLOSURE OF THE INVENTION

It has now surprisingly been found that compounds of this invention have strong selective 5-HT$_4$ agonistic activity, and thus are useful for the treatment of disease conditions mediated by 5-HT$_4$ activity such as gastroesophageal reflux disease, gastrointestinal disease, gastric motility disorder, non-ulcer dyspepsia, functional dyspepsia, irritable bowel syndrome (IBS), constipation, dyspepsia, esophagitis, gastroesophageral disease, nausea, central nervous system disease, Alzheimer's disease, cognitive disorder, emesis, migraine, neurological disease, pain, cardiovascular disorders, cardiac failure, heart arrhythmia, diabetes and apnea syndrome (especially caused by an opioid administration).

Further, the compounds of the present invention show a reduced QT prolongation by introducing a polar group into $R^3$ of the formula (I). QT prolongation is known to have a potential liability to produce fatal cardiac arrhythmias of Torsades de Pointes (TdP). The ability to prolong the cardiac action potential duration was identified as being due to an action at the HERG potassium channel. For example, drugs withdrawn from the market due to QT prolongation, such as Cisapride and Terfenadine, are known to be potent HERG potassium channel blocker (Expert Opinion of Pharmacotherapy.; 2, pp 947-973, 2000) Inhibitory activity at HERG channel was estimated from affinity for HERG type potassium channel was investigated by checking [$^3$H]dofetilide binding, which can predict inhibitory activity at HERG channel (Eur. J. Pharmacol., 430, pp 147-148, 2001).

The compounds of the present invention may show less toxicity, good absorption, distribution, good solubility, low protein binding affinity, less drug-drug interaction, and good metabolic stability.

The present invention provides a compound of the following formula (I) or a pharmaceutically acceptable salt thereof.

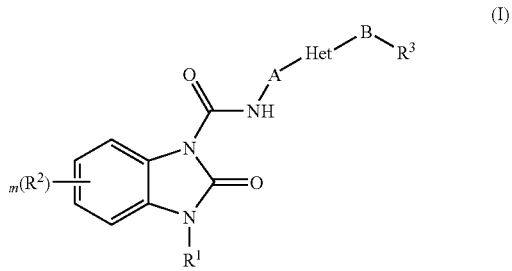

wherein
Het represents a heterocyclic group having one nitrogen atom, to which B binds directly, and from 4 to 7 carbon atoms, and said heterocyclic group being unsubstituted or substituted by 1 to 4 substituents independently selected from the group consisting of substituents $\alpha^1$;
A represents an alkylene group having from 1 to 4 carbon atoms;
B represents a covalent bond or an alkylene group having from 1 to 5 carbon atoms, and said alkylene group being unsubstituted or substituted by an oxo group when $R^3$ represents a heterocyclic group;
$R^1$ represents an isopropyl group or a cyclopentyl group;

$R^2$ independently represents a halogen atom or an alkyl group having from 1 to 4 carbon atoms; m is 0, 1, 2, 3 or 4; and
$R^3$ represents
(i) a cycloalkyl group having from 3 to 8 carbon atoms, and said cycloalkyl group being substituted by 1 to 5 substituents independently selected from the group consisting of substituents $\alpha^2$, or
(ii) a heterocyclic group having from 3 to 8 atoms, and said heterocyclic group being unsubstituted or substituted by 1 to 5 substituents independently selected from the group consisting of substituents β,
said substituents $\alpha^1$ are independently selected from a hydroxy group and an amino group;
said substituents $\alpha^2$ are independently selected from a hydroxy group, an amino group, a hydroxy-substituted alkyl group having from 1 to 4 carbon atoms, a carboxyl group and an alkoxy group having from 1 to 4 carbon atoms; and
said substituents β are independently selected from a hydroxy group, a hydroxy-substituted alkyl group having from 1 to 4 carbon atoms, a carboxyl group, an amino group, an alkyl group having from 1 to 4 carbon atoms, an amino-substituted alkyl group having from 1 to 4 carbon atoms and a carbamoyl group.

The invention also provides a compound of the formula (I):

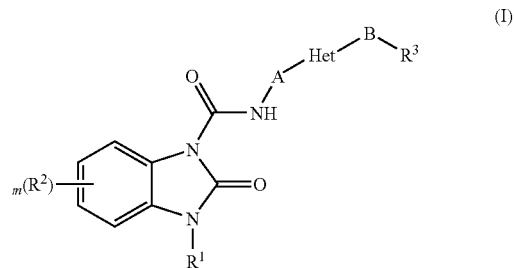

or a pharmaceutically acceptable salt thereof, wherein:
Het represents a heterocyclic group having one nitrogen atom, to which B binds directly, and from 4 to 7 carbon atoms, and said heterocyclic group being unsubstituted or substituted by 1 to 4 substituents independently selected from the group consisting of substituents $\alpha^1$;
A represents an alkylene group having from 1 to 4 carbon atoms;
B represents a covalent bond or an alkylene group having from 1 to 5 carbon atoms, and said alkylene group being unsubstituted or substituted by an oxo group when $R^3$ represents a heterocyclic group;
$R^1$ represents an isopropyl group or a cyclopentyl group;
$R^2$ independently represents a halogen atom or an alkyl group having from 1 to 4 carbon atoms; m is 0, 1, 2, 3 or 4; and
$R^3$ represents
(i) a cycloalkyl group having from 3 to 8 carbon atoms, and said cycloalkyl group being substituted by 1 to 5 substituents independently selected from the group consisting of substituents $\alpha^2$, or
(ii) a heterocyclic group having from 3 to 8 atoms, and said heterocyclic group being unsubstituted or substituted by 1 to 5 substituents independently selected from the group consisting of substituents β,
said substituents $\alpha^1$ are independently selected from a hydroxy group and an amino group;
said substituents $\alpha^2$ are independently selected from a hydroxy group, an amino group, a hydroxy-substituted alkyl group having from 1 to 4 carbon atoms, a carboxyl-substituted alkyl group having 1 to 4 carbon atoms, a carboxyl group and an alkoxy group having from 1 to 4 carbon atoms; and said substituents β are independently selected from a hydroxy group, a hydroxy-substituted alkyl group having from 1 to 4 carbon atoms, a carboxyl-substituted alkyl group having 1 to 4 carbon atoms, a carboxyl group, an amino group, an alkyl group having from 1 to 4 carbon atoms, an amino-substituted alkyl group having from 1 to 4 carbon atoms and a carbamoyl group.

Also, the present invention provides a pharmaceutical composition for the treatment of disease conditions mediated by 5-HT$_4$ receptor, in a mammalian subject, which comprises administering to said subject a therapeutically effective amount of a compound of formula (I) or pharmaceutically acceptable salts thereof.

Further, the present invention also provides a pharmaceutical composition for the treatment of diseases selected from gastroesophageal reflux disease, gastrointestinal disease, gastric motility disorder, non-ulcer dyspepsia, functional dyspepsia, irritable bowel syndrome (IBS), constipation, dyspepsia, esophagitis, gastroesophageral disease, nausea, central nervous system disease, Alzheimer's disease, cognitive disorder, emesis, migraine, neurological disease, pain, cardiovascular disorders, cardiac failure, heart arrhythmia, diabetes and apnea syndrome, or the like, which comprises a therapeutically effective amount of the benzimidazolone compound of formula (I) or its pharmaceutically acceptable salt together with a pharmaceutically acceptable carrier.

Also, the present invention provides a method of the treatment of a mammal, including a human, to treat a disease conditions mediated by 5-HT$_4$ receptor, in a mammalian subject, which comprises administering to said subject a therapeutically effective amount of a compound of formula (I) or pharmaceutically acceptable salts thereof. Further, the present invention provides a method for the treatment of the disease conditions as mentioned above. Furthermore, the present invention provides use of the compound of formula (I) or pharmaceutically acceptable salts thereof in the manufacture of a medicament for the treatment of disease conditions mediated by 5-HT$_4$ receptor activity, in a mammalian subject. The conditions mediated by 5-HT$_4$ receptor activity include those diseases or disorders described as above.

Also, the present invention provides a compound of the following formula (2-A') or a salt thereof:

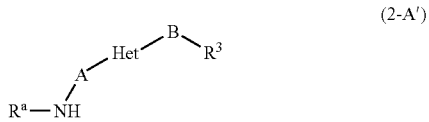

(2-A')

wherein

R$^a$ represents a hydrogen atom or a N-protecting group;

Het represents a heterocyclic group having one nitrogen atom, to which B binds directly, and from 4 to 7 carbon atoms, and said heterocyclic group being unsubstituted or substituted by 1 to 4 substituents independently selected from the group consisting of substituents α$^1$;

A represents an alkylene group having from 1 to 4 carbon atoms;

B represents a covalent bond or an alkylene group having from 1 to 5 carbon atoms, and said alkylene group being unsubstituted or substituted by an oxo group when R$^3$ represents a heterocyclic group;

R$^3$ represents
(i) a cycloalkyl group having from 3 to 8 carbon atoms, and said cycloalkyl group being substituted by 1 to 5 substituents independently selected from the group consisting of substituents α$^2$, or
(ii) a heterocyclic group having from 3 to 8 atoms, and said heterocyclic group being unsubstituted or substituted by 1 to 5 substituents independently selected from the group consisting of substituents β, said substituents α$^1$ are independently selected from a hydroxy group and an amino group;

said substituents α$^2$ are independently selected from a hydroxy group, an amino group, a hydroxy-substituted alkyl group having from 1 to 4 carbon atoms, a carboxyl group and an alkoxy group having from 1 to 4 carbon atoms; and said substituents β are independently selected from a hydroxy group, a hydroxy-substituted alkyl group having from 1 to 4 carbon atoms, a carboxyl group, an amino group, an alkyl group having from 1 to 4 carbon atoms, an amino-substituted alkyl group having from 1 to 4 carbon atoms and a carbamoyl group,

DETAILED DESCRIPTION OF THE INVENTION

As used herein, the term "heterocyclic" of "Het" means a heterocyclic group having one nitrogen atom and from 4 to 7 carbon atoms such as

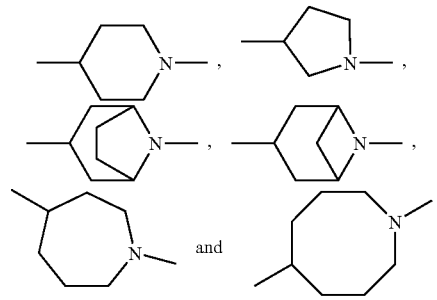

and

As used herein, the term "alkylene" in "A" means straight or branched chain saturated radicals having 1 to 4 carbon atoms, including, but not limited to methylene, ethylene, n-propylene, isopropylene, n-butylene, isobutylene, sec-butylene, tert-butylene. The "alkylene" in "A" represents preferably a methylene group, an ethylene group or a propylene group; more preferably a methylene group or an ethylene group; most preferably a methylene group.

As used herein, the term "alkylene" in "B" means straight or branched chain saturated radicals having 1 to 5 carbon atoms, including, but not limited to methylene, ethylene, n-propylene, isopropylene, n-butylene, isobutylene, sec-butylene, tert-butylene, n-pentylene, isopentylene, sec-pentylene, tert-pentylene. The "alkylene" in "B" represents preferably an alkylene group having from 1 to 4 carbon atoms; more preferably an alkylene group having from 1 to 3 carbon atoms; much more preferably a methylene group or an ethylene group; further more preferably a methylene group.

As used herein, the term "halogen" in "R$^2$" means fluoro, chloro, bromo and iodo, preferably fluoro or chloro.

As used herein, the term "alkyl" in "R$^2$"; "alkyl" of "a hydroxy-substituted alkyl group" and "an alkoxy group having from 1 to 4 carbon atoms" in "substituents $\alpha^2$"; "alkyl" in "substituents $\beta$"; and "alkyl" of "a hydroxy-substituted alkyl group" and "an amino-substituted alkyl group" in "substituents $\beta$" mean straight or branched chain saturated radicals having 1 to 4 carbon atoms, including, but not limited to methyl, ethyl, n-propyl, isopropyl, n-butyl, isobutyl, sec-butyl, ten-butyl.

As used herein, the term "cycloalkyl" in "$R^3$" means cyclic alkyl group having 3 to 8 carbon atoms, such as cyclopropyl, cyclobutyl, cyclopentyl, cyclohexyl, cycloheptyl, cyclooctyl, and etc.

As used herein, the term "heterocyclic" of "$R^3$" means a heterocyclic ring which has one or more hetero atoms in the ring, preferably has 2 to 6 carbon atoms and 1 to 3 heteroatoms, including aziridinyl, azetidinyl, piperidinyl, morpholinyl(including morpholino), pyrrolidinyl, pyrazolidinyl, piperazinyl, tetrahydropyrazolyl, pyrazolinyl, tetrahydropyranyl and etc.

The term "treating", as used herein, refers to reversing, alleviating, inhibiting the progress of, or preventing the disorder or condition to which such term applies, or one or more symptoms of such disorder or condition. The term "treatment" as used herein refers to the act of treating, as "treating" is defined immediately above.

A preferred compound of formula (I) of this invention is that wherein Het represents a heterocyclic group selected from

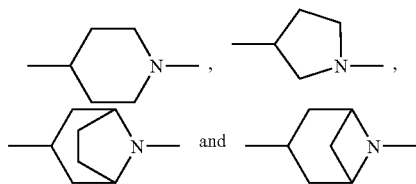

said heterocyclic group being unsubstituted or substituted by 1 to 3 substituents independently selected from the group consisting of substituents $\alpha^1$; and A represents an alkylene group having from 1 to 3 carbon atoms.

A more preferred compound of formula (I) of this invention is that wherein

Het represents a group of formula

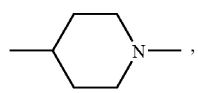

and this group being unsubstituted or substituted by one substituent selected from the group consisting of substituents $\alpha^1$;

A represents an alkylene group having from 1 to 2 carbon atoms;

B represents an alkylene group having from 1 to 4 carbon atoms, and said alkylene group being unsubstituted or substituted by an oxo group when $R^3$ represents a heterocyclic group;

$R^2$ independently represents a halogen atom or an alkyl group having from 1 to 2 carbon atoms; m is 0, 1 or 2; and $R^3$ represents
  (i) a cycloalkyl group having from 4 to 7 carbon atoms, and said cycloalkyl group being substituted by 1 to 3 substituents independently selected from the group consisting of substituents $\alpha^2$, or
  (ii) a heterocyclic group having from 4 to 7 atoms, and said heterocyclic group being unsubstituted or substituted by 1 to 3 substituents independently selected from the group consisting of substituents $\beta$.

Also, a further preferred compound of formula (I) of this invention is the compound or its pharmaceutically acceptable salt wherein Het represents a group of formula

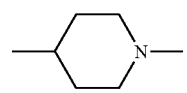

and this group being unsubstituted or substituted by one substituent selected from the group consisting of substituents $\alpha^1$;

A represents a methylene group;

B represents an alkylene group having from 1 to 2 carbon atoms;

$R^1$ represents an isopropyl group;

$R^2$ independently represents a fluorine atom, a chlorine atom or a methyl; and $R^3$ represents
  (i) a cycloalkyl group having from 5 to 7 carbon atoms, and said cycloalkyl group being substituted by 1 to 2 substituents independently selected from the group consisting of substituents $\alpha^2$, or
  (ii) a heterocyclic group having from 5 to 7 atoms, and said heterocyclic group being unsubstituted or substituted by 1 to 2 substituents independently selected from the group consisting of substituents $\beta$, said substituents $\alpha^2$ are independently selected from a hydroxy group, an amino group and an alkoxy group having from 1 to 2 carbon atoms; and said substituents $\beta$ are independently selected from a hydroxy group, a hydroxy-substituted alkyl group having from 1 to 2 carbon atoms, a carboxyl group, an amino group, an amino-substituted alkyl group having from 1 to 2 carbon atoms and a carbamoyl group.

A further preferred compound of formula (I) of this invention is the compound or its pharmaceutically acceptable salt wherein Het represents a group of formula

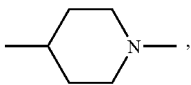

A represents a methylene group;
B represents a methylene group;
$R^1$ represents an isopropyl group;
$R^2$ represents a fluorine atom; m is 0 or 1; and
$R^3$ represents
  (i) a cycloalkyl group having from 5 to 6 carbon atoms, and said cycloalkyl group being substituted by 1 to 2 substituents independently selected from the group consisting of substituents $\alpha^2$, or
  (ii) a heterocyclic group having from 5 to 6 atoms, and said heterocyclic group being unsubstituted or substituted by 1 to 2 substituents independently selected from the group consisting of substituents β,
said substituents α² are independently selected from a hydroxy group and an amino group; and
said substituents β are independently selected from a hydroxy group and an amino group.

A further preferred compound of formula (I) of this invention is the compound or its pharmaceutically acceptable salt, wherein
Het represents a group of formula

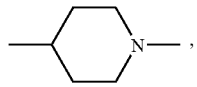

A represents a methylene group;
B represents a methylene group;
R¹ represents an isopropyl group;
R² represents a fluorine atom; m is 0; and
R³ represents
  (i) a cyclohexyl group substituted by 1 to 2 substituents independently selected from a hydroxy group or an amino group, or
  (ii) a heterocyclic group having from 6 atoms, and said heterocyclic group being substituted by a hydroxy group or an amino group.

Most preferred compounds of formula (I) of this invention is the compound or its pharmaceutically acceptable salt, wherein
Het represents a group of formula

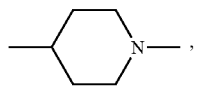

A represents a methylene group;
B represents a methylene group;
R¹ represents an isopropyl group;
R² represents a fluorine atom; m is 0; and
R³ represents
  (i) a cyclohexyl group substituted by 1 or 2 hydroxy group (especially dihydroxycyclohexyl), or
  (ii) a tetrahydropyran group substituted by 1 or 2 hydroxy group (especially hydroxytetrahydropyranyl).

In the compounds of formula (I) or the pharmaceutically acceptable salt, R² preferably represents a fluorine atom, a chlorine atom, a methyl group or an ethylene group; more preferably a fluorine atom, a chlorine atom, a methyl group; most preferably a fluorine atom.

In the compounds of formula (I) or the pharmaceutically acceptable salt, m is preferably 0, 1 or 2; more preferably 0 or 1; much more preferably 0.

Preferred individual compound of this invention is:
N-({1-[(4-hydroxytetrahydro-2H-pyran-4-yl)methyl]piperidin-4-yl}methyl)-3-isopropyl-2-oxo-2,3-dihydro-1H-benzimidazole-1-carboxamide;
N-({1-[(trans-1,4-dihydroxyhexyl)methyl]piperidin-4-yl}methyl)-3-isopropyl-2-oxo-2,3-dihydro-1H-benzimidazole-1-carboxamide;
N-({1-[(cis-1,4-dihydroxyhexyl)methyl]piperidin-4-yl}methyl)-3-isopropyl-2-oxo-2,3-dihydro-1H-benzimidazole-1-carboxamide;
6-fluoro-N-({1-[(4-hydroxytetrahydro-2H-pyran-4-yl)methyl]piperidin-4-yl}methyl)-3-isopropyl-2-oxo-2,3-dihydro-1H-benzimidazole-1-carboxamide;
4-{[4-({[(3-isopropyl-2-oxo-2,3-dihydro-1H-benzimidazol-1-yl)carbonyl]amino}methyl)piperidin-1-yl]methyl}tetrahydro-2H-pyran-4-carboxylic acid;
1-{[4-({[(3-isopropyl-2-oxo-2,3-dihydro-1H-benzimidazol-1-yl)carbonyl]amino}methyl)piperidin-1-yl]methyl}cyclopentanecarboxylic acid; and
1-{[4-({[(3-isopropyl-2-oxo-2,3-dihydro-1H-benzimidazol-1-yl)carbonyl]amino}methyl)piperidin-1-yl]methyl}cyclobutanecarboxylic acid;

or a pharmaceutically acceptable salt thereof.

A preferred compound of formula (2-A') of this invention is that wherein
R^a represents a hydrogen atom or a t-butoxycarbonyl group;
Het represents a group of formula

A represents an methylene group; B represents an methylene group; and
R³ represents hydroxytetrahydropyranyl or dihydroxycyclohexyl.

General Synthesis

The compounds of the present invention may be prepared by a variety of processes well known for the preparation of compounds of this type, for example as shown in the following reaction Schemes. Unless otherwise indicated R¹ through R³ and m in the following reaction Schemes and discussion are defined as above. The term "protecting group", as used hereinafter, means a hydroxy or amino protecting group which is selected from typical hydroxy or amino protecting groups described in Protective Groups in Organic Synthesis edited by T. W. Greene et al. (John Wiley & Sons, 1991); All starting materials in the following general syntheses may be commercially available or obtained by conventional methods known to those skilled in the art.

The compound of formula (I), wherein Het is

is prepared by the following synthesis. And the compound of formula (I), wherein Het is other than

can be prepared by a similar manner or a method known to a skilled person.

In Steps 1a, 1b, 1d, 2a, 2c, 2e, 3a, 3c, 3d of the following schemes, each reaction is preferably carried out in the presence of a base. There is no particular restriction on the nature of the bases used, and any base commonly used in reactions of this type may equally be used here. The base employed includes, for example, alkali metal hydroxides, such as lithium hydroxide, sodium hydroxide and potassium hydroxide; alkali metal carbonates such as sodium carbonate and potassium carbonate; alkali metal hydrides such as sodium hydride, potassium hydride and lithium hydride; alkali metal alkoxides such as sodium methoxide, sodium ethoxide, potassium t-butoxide and lithium methoxide; alkyllithiums such as butyllithium and methyllithium; lithium amides such as lithium diethylamides, lithium diisopropylamide and lithium bis(trimethylsilyl)amide; alkali metal hydrogencarbonates such as sodium hydrogencarbonate and potassium hydrogencarbonate; and tertiary organic amines such as triethylamine, dimethylaniline, pyridine, 4-dimethylaminopyridine, 1,5-diazabicyclo[4.3.0]non-5-ene, 1,8-diazabicyclo[5.4.0]undec-7-ene and N,N-diisopropylethylamine.

Synthesis of Benzimidazolone (1-A):

The following reaction Schemes illustrate the preparation of benzimidazolone compounds of formula 1-A.

Scheme 1a:

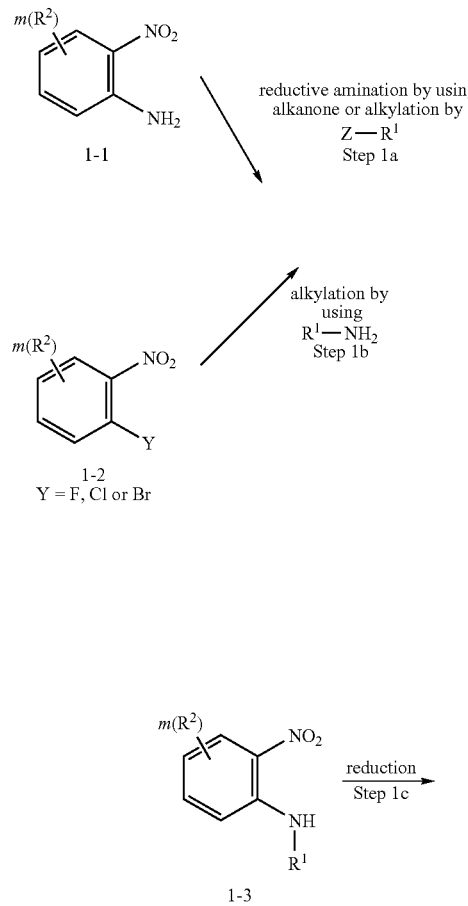

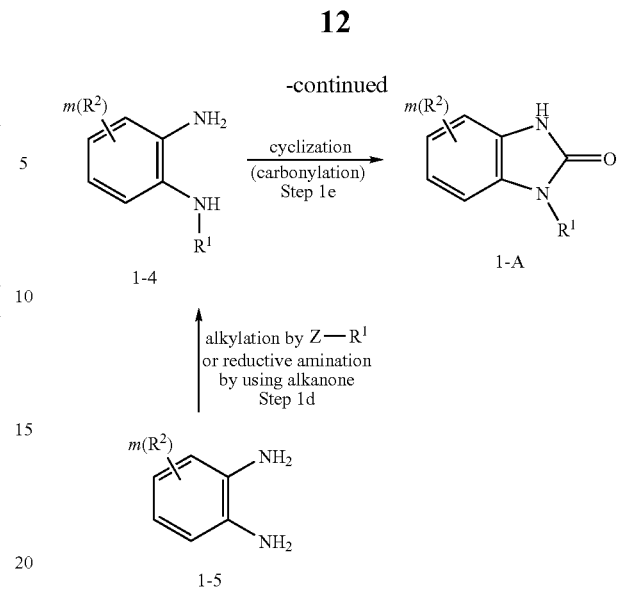

In the above formulae, Z represents 'halo', such as a chlorine, bromine or iodine atom.

Step 1a

In step 1a, an amine compound of formula 1-3 can be prepared by the reductive amination of the alkanone compound (having from 1 to 4 carbon atoms) with an amine compound of formula 1-1 in the presence or absence of a reducing agent or a metal agent in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable aqueous or non-aqueous organic solvents include: alcohols, such as methanol, ethanol or isopropanol; ethers, such as tetrahydrofuran (THF), dimethoxyethane or dioxane; acetonitrile; N,N'-dimethylformamide; dimethylsulfoxide; acetic acid; and halogenated hydrocarbon, such as dichloromethane, dichloroethane or chloroform.

The reaction can take place over a wide range of temperatures, and the precise reaction temperature is not critical to the invention. The preferred reaction temperature will depend upon such factors as the nature of the solvent, and the starting material or reagent used. However, in general, it is convenient to carry out the reaction with reducing agents at a temperature of from −78° C. to 100° C., more preferably from about −20° C. to 60° C. The time required for the reaction may also vary widely, depending on many factors, notably the reaction temperature and the nature of the reagents and solvent employed. However, provided that the reaction is effected under the preferred conditions outlined above, a period of 5 minutes to 1 week, more preferably 30 minutes to 24 hours, will usually suffice. In the case of the reaction with metal reagents, it is convenient to carry out the reaction at a temperature of from 20° C. to 100° C., preferably from about 20° C. to 60° C. for 10 minutes to 48 hours, preferably 30 minutes to 24 hours.

Suitable reducing reagents are those typically used in the reduction including, for example, sodium borohydride, sodium cyanoborohydride or sodium triacetoxyborohydride.

The combination of metal reagents and hydrogen gas can be also employed as reducing reagent. Example of suitable metal reagents include palladium-carbon, palladiumhydroxide-carbon, platinumoxide, platinum-carbon, ruthenium-carbon, rhodium-aluminumoxide and tris[triphenyphosphine]

rhodiumchloride. The reduction with metal reagents may be carried out under hydrogen atmosphere at a pressure ranging from 1 to 100 atm, preferably from 1 to 10 atm.

This reduction can be carried out after formation of the corresponding enamine of the alkanone compound or imine of the alkanone compound in a reaction-inert solvent such as benzene, toluene, or xylene at a temperature in the range from 20 to 130° C. for 1 hour to 1 week.

Alternatively, the compound of formula 1-3 can be prepared by alkylation of the compound of formula 1-1 with an alkyl halide of formula of Z—$R^1$ wherein Z is halo (halo is chloro, bromo, or iodo) as essentially the same condition as below (Step 1d), preferably in the presence of a base.

Step 1b

In this step, a compound of formula 1-3 can be prepared by alkylation of a compound of formula 1-2 with compound of formula $R^1$—$NH_2$.

The reaction can take place over a wide range of temperatures, and the precise reaction temperature is not critical to the invention. The preferred reaction temperature will depend upon such factors as the nature of the solvent, and the starting material or reagent used. However, in general, it is convenient to carry out the reaction at a temperature of from 0° C. to 150° C., more preferably from 20° C. to 120° C. The time required for the reaction may also vary widely, depending on many factors, notably the reaction temperature and the nature of the reagents and solvent employed. However, provided that the reaction may be effected under the preferred conditions outlined above, a period of from 5 minutes to 48 hours, more preferably from 30 minutes to 24 hours, will usually suffice.

Step 1c

A compound of formula 1-4 can be prepared by reduction of a compound of formula 1-3 with a suitable reducing agent, such as sodium borohydride ($NaBH_4$), lithium aluminumhydride (LAH), diborane, hydrogen and a metal catalyst, iron and hydrochoric acid, stannic chloride and hydrochoric acid, zinc and hydrochoric acid, formic acid, borane dimethylsulfide complex, borane-THF, (preferably hydrogen and a metal catalyst), usually in excess, in a reaction inert solvent such as methanol, ethanol, propanol, butanol, terahydrofuran (THF) (preferably methanol or ethanol), generally at temperature of −78° C. to 60° C., preferably from about 0° C. to 45° C. for 5 minutes to 24 hours, preferably 60 minutes to 12 hours.

Step 1d

In step 1d, an amine compound of formula 1-4 can be prepared by the reductive amination of the alkanone compound with an amine compound of formula 1-5 in a similar condition in step 1a.

Alternatively, a compound of formula 1-4 can be prepared by alkylation of a compound of formula 1-5 with compound of formula Z—$R^1$.

The reaction can take place over a wide range of temperatures, and the precise reaction temperature is not critical to the invention. The preferred reaction temperature will depend upon such factors as the nature of the solvent, and the starting material or reagent used. However, in general, it is convenient to carry out the reaction at a temperature of from 0° C. to 120° C., more preferably from 0° C. to 70° C. The time required for the reaction may also vary widely, depending on many factors, notably the reaction temperature and the nature of the reagents and solvent employed. However, provided that the reaction may be effected under the preferred conditions outlined above, a period of from 5 minutes to 48 hours, more preferably from 30 minutes to 24 hours, will usually suffice.

Step 1e

A compound of formula 1-A can be prepared by cyclization of a compound of formula 1-4 with a suitable carbonylating agent such as carbonyldiimidazole, trichloromethyl chloroformate, triphosgene and urea (preferably carbonyldiimidazole), usually in excess, in a reaction inert solvent such as dimethoxyethane, dioxane, acetonitrile, N,N'-dimethylformamide, dimethylsulfoxide, dichloromethane, dichloroethane, chloroform, or terahydrofuran (THF) (preferably THF), generally at temperature of −78° C. to 120° C., preferably from about 20° C. to 100° C. for 5 minutes to 24 hours, preferably 60 minutes to 12 hours.

Alternatively, the compound of 1-A (wherein $R^1$ is isopropyl as shown in Scheme 1b) can be prepared from an alkenylbenzimidazolone compound of formula 1-6 according to the following Scheme 1b in a reaction condition known to a skilled person.

Scheme 1b:

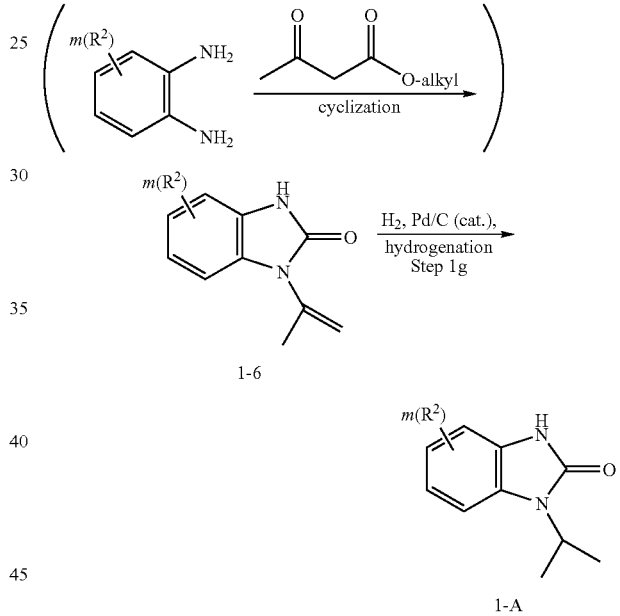

Synthesis of Amine Moiety (2-A):

The following reaction Schemes illustrate the preparation of piperidine compounds of formula (2-A).

Scheme 2a:

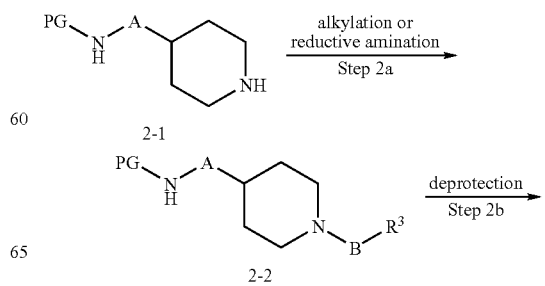

15

-continued

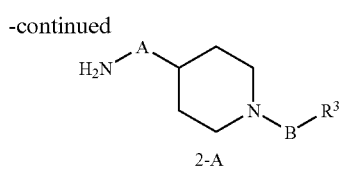

2-A

In the above formulae, PG represents a protecting group. The term "protecting group", as used herein, means an amino protecting group which is selected from typical amino protecting groups described in Protective Groups in Organic Synthesis edited by T. W. Greene et al. (John Wiley & Sons, 1991). Typical amino protecting groups include benzyl, $C_2H_5O(C=O)-$, $CH_3(C=O)-$, tert-butyldimethylsilyl (TBS), tert-butyldiphenylsilyl, benzyloxycarbonyl represented as Z and tert-buthoxycarbonyl represented as t-Boc or Boc.

A compound of formula 2-2 can be prepared by alkylation or reductive amination of a compound of formula 2-1 with a compound of formula alkyl-$R^3$, halo-$R^3$, or $H(C=O)-R^3$ in a similar condition to step 1a. When $-B-R^3$ represents 4-hydroxytetrahydropyranylmethyl, this alkylation can be done by using a 1,6-dioxaspiro[2.5]octane compound.

Then, this reaction is followed by deprotection to obtain a compound of formula 1-A. This deprotection may be carried out according to procedures known to those skilled in the art to give the compound of formula of 2-A.

Alternatively, the compound of formula (2-A) can be prepared from a piperidine compound of formula 2-3 according to the following Scheme 2b with a reaction condition known to a skilled person.

Scheme 2b:

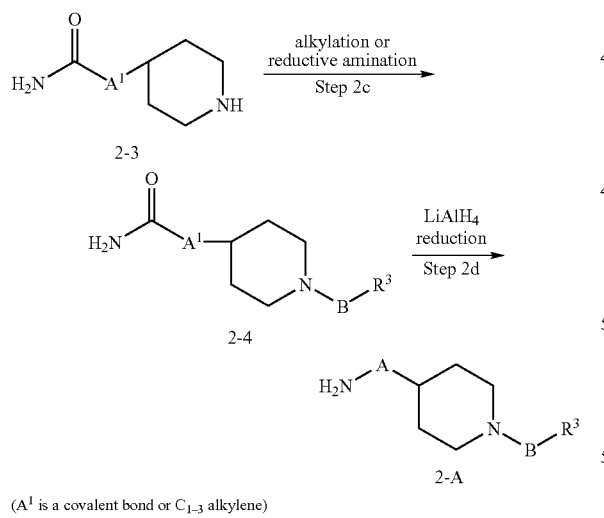

($A^1$ is a covalent bond or $C_{1-3}$ alkylene)

For example, in step 2c, the compound 2-4 may be prepared by alkylation or reductive amination in essentially the same condition as one described in step 2a of Scheme 2a. Then, the reduction in step 2d may be carried out in the presence of a reducing reagent such as LiAlH$_4$ in a reaction inert solvent such as THF. Suitable reaction temperature ranges from about −78° C. to about 100° C., preferably from about −30° C. to about 40° C.

16

The compound of formula (1-A) can be prepared from a piperidine compound of formula 2-5 according to the following Scheme 2c with a reaction condition known to a skilled person Scheme 2c:

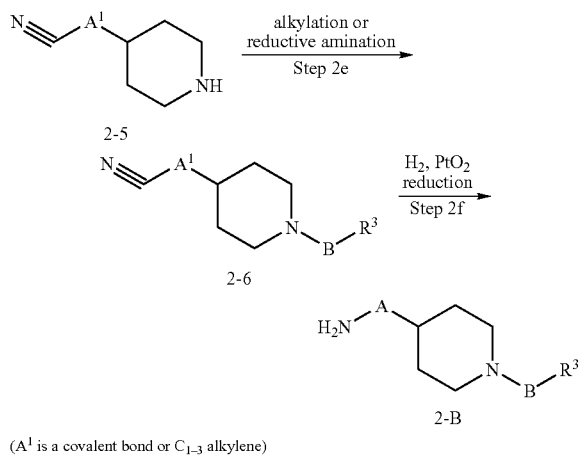

($A^1$ is a covalent bond or $C_{1-3}$ alkylene)

For example, in step 2e, the compounds 2-6 may be prepared by alkylation or reductive amination in a similar condition to one described in step 2a of scheme 2a. Then, the reduction in step 2f may be carried out in the presence of a H$_2$ and a hydrogenation catalyst such as PtO$_2$ in a reaction inert solvent such as THF. Suitable reaction temperature ranges from about −78° C. to about 100° C., preferably from about −30° C. to about 40° C.

Synthesis of the Compound of Formula (I):

The following reaction Schemes illustrate the preparation of benzimidazolone compounds of formula I.

Scheme 3a:

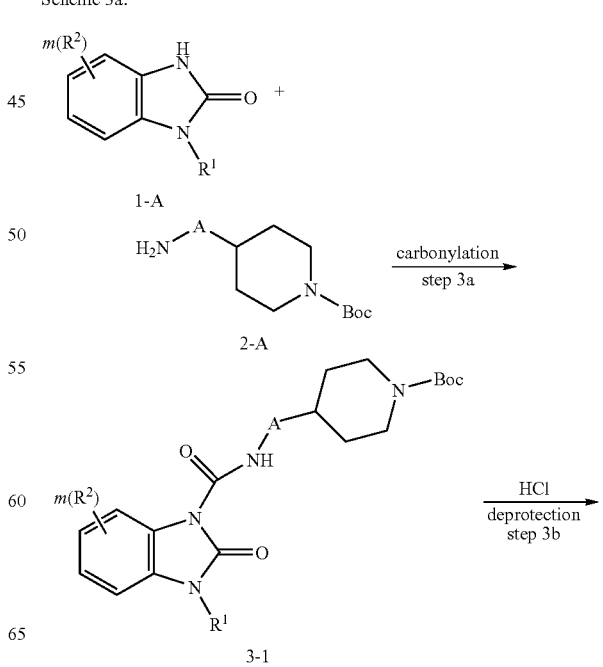

17

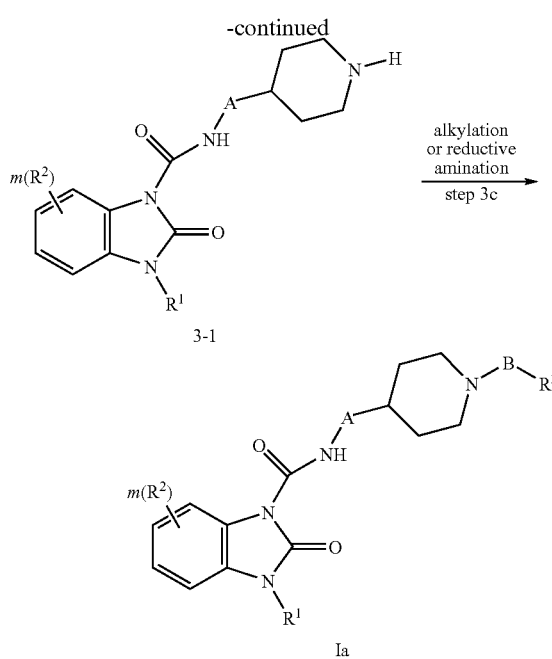

3-1

Ia

Alternatively, the compound of formula (Ia) can be prepared from alkyl-benzimidazolone compounds according to the following Scheme 3b in a reaction condition known to a skilled person.

Scheme 3a:

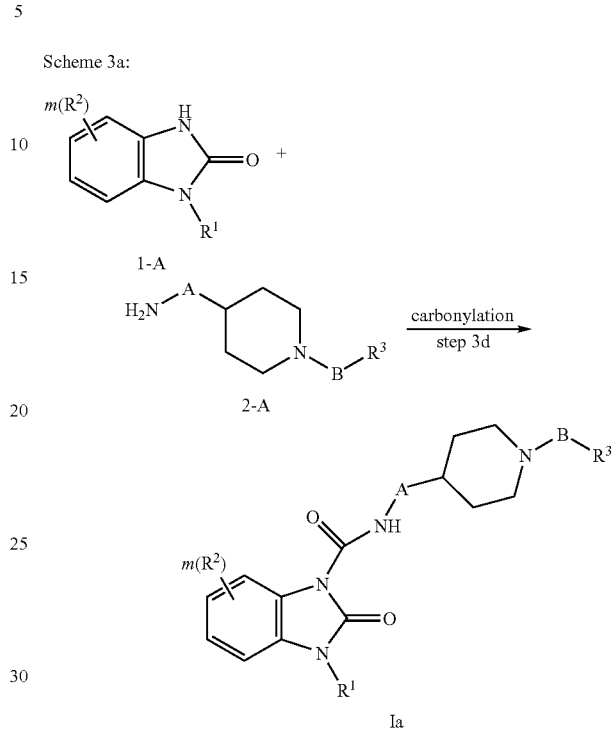

1-A

2-A

Ia

Step 3a:

A compound of formula 3-1 can be prepared by carbonylation of a compound of formula 1-A with a compound of formula 2-A in the presence of a suitable carbonylating agent such as carbonyldiimidazole, trichloromethyl chloroformate, triphosgene, 4-nitrophenyl chloroformate, or urea (preferably triphosgene), usually in excess, in a reaction inert solvent such as, dimethoxyethane, dioxane, acetonitrile, N,N'-dimethylformamide, dimethylsulfoxide, dichloromethane, dichloroethane, terahydrofuran (THF), benzene, toluene, or chloroform (preferably THF), generally at temperature of −78° C. to 120° C., preferably from about 0° C. to 90° C. for 5 minutes to 24 hours, preferably 60 minutes to 12 hours.

Step 3b:

A compound of formula 3-2 is prepared by deprotection of a compound of formula 3-1 with an acid such as hydrochloride, Step 3c:

A compound of formula (Ia) can be prepared by alkylation or reductive amination in a similar condition to one described in step 2a of Scheme 2a.

For example, in step 3d, the compound of formula 1-A can be reacted with a compound of formula 2-A in the presence of a carbonylating agent such as carbonyldiimidazole, trichloromethyl chloroformate, triphosgene, 4-nitrophenyl chloroformate, or urea (preferably triphosgene), usually in excess, in a reaction inert solvent such as dimethoxyethane, dioxane, acetonitrile, N,N'-dimethylformamide, dimethylsulfoxide, dichloromethane, dichloroethane, terahydrofuran (THF), benzene, toluene, or chloroform (preferably THF), generally at temperature of −78° C. to 120° C., preferably from about 0° C. to 90° C. for 5 minutes to 24 hours, preferably 60 minutes to 12 hours.

The compound of formula 7 can be prepared by using a reaction known to a skilled person. For example, the compound of formula 7 can be prepared from a compound of formula 3 according to the following Scheme 3c in a reaction condition known to a skilled person.

Scheme 3c:

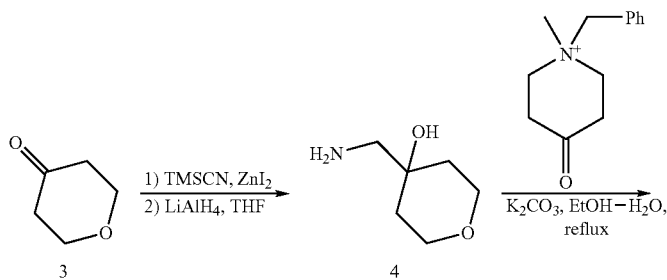

-continued

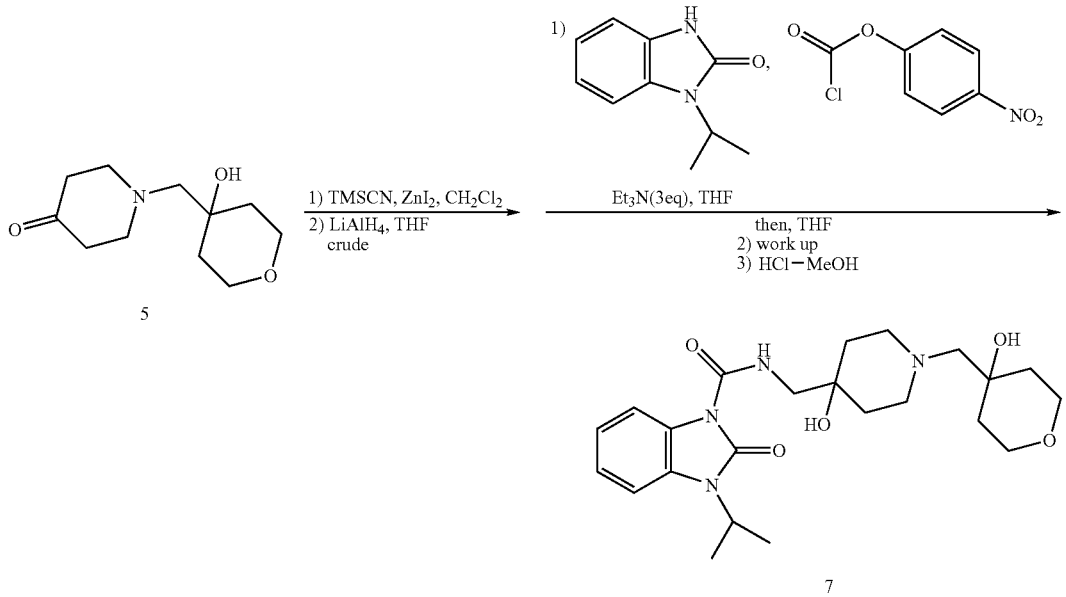

In the above Schemes from 1a to 3c, examples of suitable solvents include a mixture of any two or more of those solvents described in each Step.

The compounds of formula (I), and the intermediates above-mentioned preparation methods can be isolated and purified by conventional procedures, such as distillation, recrystallization or chromatographic purification.

The optically active compounds of this invention can be prepared by several methods. For example, the optically active compounds of this invention may be obtained by chromatographic separation, enzymatic resolution or fractional crystallization from the final compounds.

Several compounds of this invention possess an asymmetric center. Hence, the compounds can exist in separated (+)- and (−)-optically active forms, as well as in racemic one thereof. The present invention includes all such forms within its scope. Individual isomers can be obtained by known methods, such as optically selective reaction or chromatographic separation in the preparation of the final product or its intermediate.

The subject invention also includes isotopically-labelled compounds, which are identical to those recited in formula (I), but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, pharmaceutically acceptable esters of said compounds and pharmaceutically acceptable salts of said compounds, of said esters or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assay. Tritiated, i.e., $^{3}H$, and carbon-14, i.e., $^{14}C$, isotopes are particularly preferred for their ease of presentation and detectability. Further, substitution with heavier isotopes such as deuterium, i.e., $^{2}H$, can afford therapeutic advantage resulting from greater metabolic stability, for example increased in vivo half-life or reduced dosage requirement and, hence, may be preferred in some circumstances. Isotopically labeled compounds of formula (I) of this invention and prodrugs thereof can generally be prepared by carrying out the procedure disclosed in above-disclosed Schemes and/or Examples and Preparations below, by submitting a readily available isotopically labeled reagent for a non-isotopically labeled reagent.

The present invention includes salt forms of the compounds (I) as obtained.

Pharmaceutically acceptable salts of the compounds of formula (I) include the acid addition and base addition salts (including disalts) thereof.

Pharmaceutically acceptable non-toxic salts of compounds of formula (I) may be prepared by conventional techniques by, for example, contacting said compound with a stoichiometric amount of an appropriate alkali or alkaline earth metal (sodium, potassium, calcium and magnesium) hydroxide or alkoxide in water or an appropriate organic solvent such as ethanol, isopropanol, mixtures thereof, or the like.

The bases which are used to prepare the pharmaceutically acceptable base addition salts of the acidic compounds of this invention of formula (I) are those which form non-toxic base addition salts, i.e., salts containing pharmaceutically acceptable cations, such as adenine, arginine, cytosine, lysine, benethamine (i.e., N-benzyl-2-phenyletylamine), benzathine (i.e., N,N-dibenzylethylenediamine), choline, diolamine (i.e., diethanolamine), ethylenediamine, glucosamine, glycine, guanidine, guanine, meglumine (i.e., N-methylglucamine), nicotinamide, olamine (i.e., ethanolamine), ornithine, procaine, proline, pyridoxine, serine, tyrosine, valine and tromethamine (i.e., tris or tris(hydroxymethyl)aminomethane). The base addition salts can be prepared by conventional procedures.

Insofar as the certain compounds of this invention are basic compounds, they are capable of forming a wide variety of different salts with various inorganic and organic acids.

The acids which are used to prepare the pharmaceutically acceptable acid addition salts of the basic compounds of this invention of formula (I) are those which form non-toxic acid addition salts, i.e., salts containing pharmaceutically acceptable anions, such as the chloride, bromide, iodide, nitrate, sulfate or bisulfate, phosphate or acid phosphate, acetate, lactate, citrate or acid citrate, tartrate or bi-tartrate, succinate, malate, fumarate, gluconate, saccharate, benzoate, methanesulfonate, ethanesulfonate, benzenesulfonate, p-toluenesulfonate, adipate, aspartate camsylate, edisylate (i.e., 1,2-ethanedisulfonate), estolate (i.e., laurylsulfate), gluceptate (i.e., gluscoheptonate), gluconate, 3-hydroxy-2-naphthoate, xionofoate (i.e., 1-hydroxy-2-naphthoate), isethionate, (i.e., 2-hydroxyethanesulfonate), mucate (i.e., galactarate), 2-naphsylate (i.e., naphthalenesulphonate, stearate, cholate, glucuronate, glutamate, hippurate, lactobionate, lysinate, maleate, mandelate, napadisylate, nicatinate, polygalacturonate, salicylate, sulphosalicylate, tannate, tryptophanate, borate, carbonate, oleate, phthalate and pamoate (i.e., 1.1'-methylene-bis-(2-hydroxy-3-naphthoate). Of these, we prefer edisylate (including hemi-edisylate) and hydrochloride. The acid addition salts can be prepared by conventional procedures.

For a review of on suitable salts see Berge et al., J. Pharm. Sci., 66, 1-19, 1977.

The present invention includes salt forms of the compounds of formula (2-A') as obtained.

Compounds of formula (2-A') may be capable of forming cations. Cations of compounds of formula (2-A') may be prepared by conventional techniques by, for example, contacting said compound with a stoichiometric amount of an appropriate alkali or alkaline earth metal (sodium, potassium, calcium and magnesium) hydroxide or alkoxide in water or an appropriate organic solvent such as ethanol, isopropanol, mixtures thereof, or the like.

The bases used to prepare the base addition salts of the acidic compounds of formula (2-A') are those which form base addition salts. Such base addition salts include pharmaceutically acceptable base addition salts as described above and salts containing cations, such as. triethylamine, pyridine and ammonia.

The compounds of formula (2-A') are capable of forming a wide variety of different salts with various inorganic and organic acids.

The acids used to prepare the acid addition salts of the compound of formula (2-A') are those which form acid addition salts. Such acid addition salts include pharmaceutically acceptable acid addition salts as described above and salts containing anions, such as cyanide.

Also included within the scope of this invention are bio-precursors (also called pro-drugs) of the compounds of the formula (I). A bioprecursor of a compound of the formula (I) is a chemical derivative thereof which is readily converted back into the parent compound of the formula (I) in biological systems. In particular, a bioprecursor of a compound of the formula (I) is converted back to the parent compound of the formula (I) after the bioprecursor has been administered to, and absorbed by, a mammalian subject, e.g., a human subject. For example, it is possible to make a bioprecursor of the compounds of formula (I) in which one or both of L and W include hydroxy groups by making an ester of the hydroxy group. When only one of L and W includes hydroxy group, only mono-ester is possible. When both L and W include hydroxy, mono- and di-esters (which can be the same or different) can be made. Typical esters are simple alkanoate esters, such as acetate, propionate, butyrate, etc. In addition, when L or W includes a hydroxy group, bioprecursors can be made by converting the hydroxy group to an acyloxymethyl derivative (e.g., a pivaloyloxymethyl derivative) by reaction with an acyloxymethyl halide (e.g., pivaloyloxymethyl chloride).

When the compounds of the formula (I) of this invention may form solvates such as hydrates, such solvates are included within the scope of this invention.

Compounds of formula (I) containing one or more asymmetric carbon atoms can exist as two or more stereoisomers. Where a compound of formula (I) contains an alkenyl or alkenylene group, geometric cis/trans (or Z/E) isomers are possible. Where the compound contains, for example, a keto or oxime group or an aromatic moiety, tautomeric isomerism ('tautomerism') can occur. It follows that a single compound may exhibit more than one type of isomerism.

Included within the scope of the present invention are all stereoisomers, geometric isomers and tautomeric forms of the compounds of formula (I), including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Stereoisomeric conglomerates may be separated by conventional techniques known to those skilled in the art—see, for example, "Stereochemistry of Organic Compounds" by E L Eliel (Wiley, New York, 1994).

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001).

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 wt % to 5 wt % of the tablet, and glidants may comprise from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 wt % to 10 wt %, preferably from 0.5 wt % to 3 wt % of the tablet.

Other possible ingredients include anti-oxidants, colourants, flavouring agents, preservatives and taste-masking agents.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in "Pharmaceutical Dosage Forms: Tablets, Vol. 1", by H. Lieberman and L. Lachman, Marcel Dekker, N.Y., N.Y., 1980 (ISBN 0-8247-6918-X).

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Verma et al, Pharmaceutical Technology On-line, 25(2), 1-14 (2001). The use of chewing gum to achieve controlled release is described in WO 00/35298.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA micro spheres.

Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958 by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 1 to 100 µg of the compound of formula (I). The overall daily dose will typically be in the range 50 µg to 20 mg which may be administered in a single dose or, more usually, as divided doses throughout the day.

Rectal/Intravaginal Administration

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Ocular/Aural Administration

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Kit-of-Parts

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

Dosage

For administration to human patients, the total daily dose of the compounds of the invention is typically in the range 0.05 mg to 100 mg depending, of course, on the mode of administration, preferred in the range 0.1 mg to 50 mg and more preferred in the range 0.5 mg to 20 mg. For example, oral administration may require a total daily dose of from 1 mg to 20 mg, while an intravenous dose may only require from 0.5 mg to 10 mg. The total daily dose may be administered in single or divided doses.

These dosages are based on an average human subject having a weight of about 65 kg to 70 kg. The physician will readily be able to determine doses for subjects whose weight falls outside this range, such as infants and the elderly.

For the avoidance of doubt, references herein to "treatment" include references to curative, palliative and prophylactic treatment.

A 5-$HT_4$ agonist of the present invention may be usefully combined with another pharmacologically active compound, or with two or more other pharmacologically active compounds, particularly in the treatment of gastroesophageal reflux disease. For example, a 5-$HT_4$ agonist, particularly a compound of the formula (I), or a pharmaceutically acceptable salt or solvate thereof, as defined above, may be administered simultaneously, sequentially or separately in combination with one or more agents selected from:

(i) histamine $H_2$ receptor antagonists, e.g. ranitidine, lafutidine, nizatidine, cimetidine, famotidine and roxatidine;

(ii) proton pump inhibitors, e.g. omeprazole, esomeprazole, pantoprazole, rabeprazole, tenatoprazole, ilaprazole and lansoprazole;

(iii) Acid pump antagonists, e.g. soraprazan, revaprazan (YH-1885), AZD-0865, CS-526, AU-2064 and YJA-20379-8;

(iv) oral antacid mixtures, e.g. Maalox®, Aludrox® and Gaviscon®;

(v) mucosal protective agents, e.g. polaprezinc, ecabet sodium, rebamipide, teprenone, cetraxate, sucralfate, chloropylline-copper and plaunotol;

(vi) GABAB agonists, e.g. baclofen and AZD-3355;

(vii) α2 agonists, e.g. clonidine, medetomidine, lofexidine, moxonidine, tizanidine, guanfacine, guanabnz, talipexole and dexmedetomidine;

(viii) Xanthin derivatives, e.g. Theophylline, aminophylline and doxofylline;

(ix) calcium channel blockers, e.g. aranidipine, lacidipine, falodipine, azelnidipine, clinidipine, lomerizine, diltiazem, gallopamil, efonidipine, nisoldipine, amlodipine, lercanidipine, bevantolol, nicardipine, isradipine, benidipine, verapamil, nitrendipine, barnidipine, propafenone, manidipine, bepridil, nifedipine, nilvadipine, nimodipine, nifedipine and fasudil;

(x) benzodiazepine agonists, e.g. diazepam, zaleplon, zolpidem, haloxazolam, clonazepam, prazepam, quazepam, flutazolam, triazolam, lormetazepam, midazolam, tofisopam, clobazam, flunitrazepam and flutoprazepam;

(xi) prostaglandin analogues, e.g. Prostaglandin, misoprostol, treprostinil, esoprostenol, latanoprost, iloprost, beraprost, enprostil, ibudilast and ozagrel;

(xii) histamine $H_3$ agonists, e.g. R-alpha-methylhistamine and BP-294;

(xiii) anti-gastric agents, e.g. Anti-gastrin vaccine, itriglumide and Z-360;

(xiv) 5-$HT_3$ antagonists, e.g. dolasetron, palonosetron, alosetron, azasetron, ramosetron, mitrazapine, granisetron, tropisetron, E-3620, ondansetron and indisetron;

(xv) tricyclic antidepressants, e.g. imipramine, amitriptyline, clomipramine, amoxapine and lofepramine;

(xvi) GABA agonists, e.g. gabapentin, topiramate, cinolazepam, clonazepam, progabide, brotizolam, zopiclone, pregabalin and eszopiclone;

(xvii) opioid analgesics, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine and pentazocine;

(xviii) somatostatin analogues, e.g. octreotide, AN-238 and PTR-3173;

(xix) Cl Channel activator: e.g. lubiprostone;

(xx) selective serotonin reuptake inhibitors, e.g. sertraline, escitalopram, fluoxetine, nefazodone, fluvoxamine, citalopram, milnacipran, paroxetine, venlafaxine, tramadol, sibutramine, duloxetine, desvenlafaxine and depocxetine;

(xxi) anticholinergics, e.g. dicyclomine and hyoscyamine;

(xxii) laxatives, e.g. Trifyba®, Fybogel®, Konsyl®, Isogel®, Regulan®, Celevac® and Normacol®;

(xxiii) fiber products, e.g. Metamucil®;

(xxiv) antispasmodics, e.g.: mebeverine;

(xxv) dopamine antagonists, e.g. metoclopramide, domperidone and levosulpiride;

(xxvi) cholinergics, e.g. neostigmine (xxvii) AChE inhibitor: galantamine, metrifonate, rivastigmine, itopride and donepezil;

(xxviii) Tachykinin (NK) antagonists, particularly NK-3, NK-2 and NK-1 e.g. antagonists, nepadutant, saredutant, talnetant, (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]naphthridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]methyl]-1,2-dihydro-3H-1,2,4-triazol-3-one (MK-869), lanepitant, dapitant and 3-[[2-methoxy-5-(trifluoromethoxy)phenyl]methylamino]-2-phenyl-piperidine (2S,3S).

Method for Assessing Biological Activities:

The 5-$HT_4$ receptor binding affinities of the compounds of this invention are determined by the following procedures.

Membrane Preparation

Pig heads were supplied from an abattoir. Striatal tissues were dissected, weighed and homogenized in 15 volumes of 50 mM ice-cold HEPES (pH 7.5) in a Polytron homogenizer (30 sec at full speed). Suspension was centrifuged at 48,000 g and 4° C. for 15 min. The resulting pellet was resuspended in an appropriate volume of 50 mM ice-cold HEPES, dispensed into aliquots and stored at −80° C. until use.

Bovine heads were also supplied from an abattoir. Striatal tissues were dissected, weighed and homogenized in 20 volumes of 50 mM ice-cold Tris-HCl (pH 7.4) in a Polytron homogenizer (30 sec at full speed). Suspension was centrifuged at 20,000 g and 4° C. for 30 min. The resulting pellet was resuspended in 15 volumes of 50 mM ice-cold Tris-HCl, homegenized and centrifuged again in the same way. The final pellet was resuspended in an appropriate volume of 50 mM Tris-HCl, dispensed into aliquots and stored at −80° C. until use.

Cerebral cortical tissues were removed from male Sprague-Dawley (SD) rats (Japan SLC), weighed and placed in 10 volumes of 50 mM ice-cold Tris-HCl (pH 7.5). This was homogenized in a Polytron homogenizer (30 sec at full speed) and subsequently centrifuged at 48,000 g and 4° C. for 15 min. The resulting pellet was resuspended in 50 mM ice-cold Tris-HCl, homegenized and centrifuged again in the same way. The final pellet was resuspended in an appropriate volume of 50 mM Tris-HCl, dispensed into aliquots and stored at −80° C. until use.

The protein concentrations of homogenates were determined by Bradford method or BCA protein method (Pierce) with BSA as a standard.

Binding Assays

Affinity of compounds for pig or bovine $5$-$HT_4$ and rat $5$-$HT_3$ receptors were assessed with using radiolabeled specific ligands, GR 113808 ({1-[2-(methylsulfonyl)ethyl]-4-piperidinyl}[methyl-3H]-1H-indole-3-carboxylate) and BRL 43694 (1-Methyl-N-(9-[methyl-3H]-9-azabicyclo[3.3.1]non-3-yl)-1H-indazole-3-caboxamide). Compounds were incubated with 25-100 pM of [$^3$H]-GR 113808 (Amersham) and 0.6-1 mg protein of pig or bovine striatal membranes suspended in a final volume of 0.8-1 ml of 50 mM Tris-HCl (pH 7.5). Nonspecific binding was determined with 10-50 μM 5-HT. The binding of 0.3 nM [$^3$H]-BRL 43694 (NEN) was measured using 400 μg protein of rat cortical membranes suspended in a final volume of 500 μl of 50 mM Tris-HCl (pH 7.5). Nonspecific binding was determined with 10 μM 5-HT.

The plates were incubated at room temperature on a plate shaker for 30 min. The assays were stopped by rapid filtration using a Brandell cell harvester through Wallac-B filters presoaked in 0.2% poly(ethylenimine) at 4° C. for 60-90 min. The filters were washed three times with 1 ml of ice-cold 50 mM HEPES, and were dried in a microwave or at room temperature. They were bagged and heated with meltilex scintillant (Wallac) or soaked in BetaplateScint (Wallac). Receptor-bound radioactivity was quantified using Big-spot counter, Betaplate counter (Wallac) or LS counter (Packard).

Human $5$-$HT_4$ Binding(1)

Human $5$-$HT_{4(d)}$ transfected HEK293 cells were prepared and grown in-house. The collected cells were suspended in 50 mM HEPES (pH 7.4 at 4° C.) supplemented with protease inhibitor cocktail (Boehringer, 1:1000 dilution) and homogenized using a hand held Polytron PT 1200 disruptor set at full power for 30 sec on ice. The homogenates were centrifuged at 40,000×g at 4° C. for 30 min. The pellets were then resuspended in 50 mM HEPES (pH 7.4 at 4° C.) and centrifuged once more in the same manner. The final pellets were resuspended in an appropriate volume of 50 mM HEPES (pH 7.4 at 25° C.), homogenized, aliquoted and stored at −80° C. until use. An aliquot of membrane fractions was used for protein concentration determination using BCA protein assay kit (PIERCE) and ARVOsx plate reader (Wallac).

For the binding experiments, 25 μl of test compounds were incubated with 25 μl of [$^3$H]-GR113808 (Amersham, final 0.2 nM) and 150 μl of membrane homogenate and WGA-SPA beads (Amersham) suspension solutions (10 μg protein and 1 mg SPA beads/well) for 60 minutes at room temperature. Nonspecific binding was determined by 1 μM GR113808 (Tocris) at the final concentration. Incubation was terminated by centrifugation at 1000 rpm. Receptor-bound radioactivity was quantified by counting with MicroBeta plate counter (Wallac).

All compounds prepared in the working examples as described below were tested by this method, and they showed Ki values from 0.3 nM to 30 nM with respect to inhibition of binding at the $5$-$HT_4$ receptor.

Human $5$-$HT_4$ Binding(2)

Human $5$-$HT_{4(d)}$ transfected HEK293 cells were prepared and grown in-house. The collected cells were suspended in 50 mM Tris buffer (pH 7.4 at 4° C.) supplemented with protease inhibitor cocktail (Boehringer, 1:1000 dilution) and homogenized using a hand held Polytron PT 1200 disruptor set at full power for 30 sec on ice. The homogenates were centrifuged at 40,000×g at 4° C. for 10 min. The pellets were then resuspended in 50 mM Tris buffer (pH 7.4 at 4° C.) and centrifuged once more in the same manner. The final pellets were resuspended in an appropriate volume of 50 mM Tris buffer (pH 7.4 at 25° C.) containing 10 mM $MgCl_2$, homogenized, aliquoted and stored at −80° C. until use. An aliquot of membrane fractions was used for protein concentration determination using BCA protein assay kit (PIERCE) and ARVOsx plate reader (Wallac).

For the binding experiments, 50 μl of test compounds were incubated with 50 μl of [$^3$H] 5-HT (Amersham, final 8.0 nM) and 400 μl of membrane homogenate (300 μg protein/tube) for 60 minutes at room temperature. Nonspecific binding was determined by 50 μM GR113808 (Tocris) at the final concentration. All incubations were terminated by rapid vacuum filtration over 0.2% PEI soaked glass fiber filter papers using BRANDEL harvester followed by three washes with 50 mM Tris buffer (pH 7.4 at 25° C.). Receptor-bound radioactivity was quantified by liquid scintillation counting using Packard LS counter.

All compounds of Examples showed $5HT_4$ receptor affinity.

Functional Assay:

The presence of $5$-$HT_4$ receptors in the rat oesophagus and the ability to demonstrate partial agonism in the TMM preparation are reported in the literature (See G. S. Baxter et al. Naunyn-Schmiedeberg's Arch Pharmacol (1991) 343: 439-446; M. Yukiko et al. JPET (1997) 283: 1000-1008; and J. J. Reeves et al. Br. J. Pharmacol. (1991) 103: 1067-1072). More specifically, partial agonist activity can be measured according to the following procedures.

Male SD rats (Charles River) weighing 250-350 g were stunned and then killed by cervical dislocation. The oesophagus was dissected from immediately proximal to the stomach (including piece of stomach to mark distal end) up to the level of the trachea and then placed in fresh Krebs' solution.

The outer skeletal muscle layer was removed in one go by peeling it away from the underlying smooth muscle layer using forceps (stomach to tracheal direction). The remaining inner tube of smooth muscle was known as the TMM. This was trimmed to 2 cm from the original 'stomach-end' and the rest discarded.

The TMMs were mounted as whole 'open' tubes in longitudinal orientation in 5 ml organ baths filled with warm (32° C.) aerated Krebs. Tissues were placed under an initial tension of 750 mg and allowed to equilibrate for 60 minutes. The tissues were re-tensioned twice at 15 minute intervals during the equilibration period. The pump flow rate was set to 2 ml/min during this time.

Following equilibration, the pump was switched off. The tissues were exposed to 1 µM carbachol and contracted and reached a steady contractile plateau within 15 minutes. Tissues were then subject to 1 µM 5-HT (this was to prime the tissues). The tissues relaxed in response to 5-HT fairly rapidly—within 1 minute. As soon as maximal relaxation has occurred and a measurement taken, the tissues were washed at maximum rate (66 ml/min) for at least 1 minute and until the original baseline (pre-carbachol and 5-HT) has returned (usually, the baseline drops below the original one following initial equilibration). The pump flow rate was reduced to 2 ml/min and the tissues left for 60 minutes.

A cumulative concentration-effect-curve (CEC) to 5-HT was constructed across the range 0.1 nM to 1 µM, in half-log unit increments (5-HT curve 1 for data analysis). Contact time between doses was 3 minutes or until plateau established. Tissues responded quicker as concentration of 5-HT in the bath increases. At the end of the curve, the tissues were washed (at maximum rate) as soon as possible to avoid desensitisation of receptors. Pump rate was reduced to 2 ml/min and the tissues left for 60 minutes.

A second CEC was carried out—either to 5-HT (for time control tissues), another $5\text{-}HT_4$ agonist (standard) or a test compound (curve 2 for data analysis). Contact time varied for other $5\text{-}HT_4$ agonists and test compounds and was tailored according to the tissues' individual responses to each particular agent. In tissues exposed to a test compound, a high concentration (1 µm) of a $5\text{-}HT_4$ antagonist (SB 203,186: 1H-Indole-3-carboxylic acid, 2-(1-piperidinyl)ethyl ester, Tocris) was added to the bath following the last concentration of test compound. This was to see if any agonist-induced relaxation (if present) could be reversed. SB 203,186 reversed 5-HT induced relaxation, restoring the tissue's original degree of carbachol-induced tone.

Agonist activity of test compounds was confirmed by pre-incubating tissues with 100 nM standard $5HT_4$ antagonist such as SB 203,186. SB 203,186 was added to the bath 5 minutes before the addition of carbachol prior to curve 2. Tissues must be 'paired' for data analysis i.e. the test compound in the absence of SB 203,186 in one tissue was compared with the test compound in the presence of SB 203,186 in a separate tissue. It was not possible to carry out a curve 3 i.e. 5-HT curve 1, followed by the test compound curve 2 (−SB 203,186), followed by the test compound curve 3 (+SB 203,186).

Agonist-Induced cAMP Elevation in Human $5\text{-}HT_{4(d)}$ Transfected HEK293 Cells Human $S\text{-}HT_{4(d)}$ transfected HEK293 cells were established in-house. The cells were grown at 37° C. and 5% $CO_2$ in DMEM supplemented with 10% FCS, 20 mM HEPES (pH 7.4), 200 µg/ml hygromycin B (Gibco), 100 units/ml penicillin and 100 µg/ml streptomycin.

The cells were grown to 60-80% confluence. On the previous day before treatment with compounds dialyzed FCS (Gibco) was substituted for normal and the cells were incubated overnight.

Compounds were prepared in 96-well plates (12.5 µl/well). The cells were harvested with PBS/1 mM EDTA, centrifuged and washed with PBS. At the beginning of the assay, cell pellet was resuspended in DMEM supplemented with 20 mM HEPES, 10 µM pargyline (Sigma) and 1 mM 3-isobutyl-1-methylxanthine (Sigma) at the concentration of $1.6 \times 10^5$ cells/ml and left for 15 minutes at room temperature. The reaction was initiated by addition of the cells into plates (12.5 µl/well). After incubation for 15 minutes at room temperature, 1% Triton X-100 was added to stop the reaction (25 µl/well) and the plates were left for 30 minutes at room temperature. Homogenous time-resolved fluorescence-based cAMP (Schering) detection was made according to the manufacturer's instruction. ARVOsx multilabel counter (Wallac) was used to measure HTRF (excitation 320 nm, emission 665 nm/620 nm, delay time 50 µs, window time 400 µs).

Data was analyzed based on the ratio of fluorescence intensity of each well at 620 nm and 665 nm followed by cAMP quantification using cAMP standard curve. Enhancement of cAMP production elicited by each compound was normalized to the amount of cAMP produced by 1000 nM serotonin (Sigma).

All compounds of Examples showed $5HT_4$ receptor agonistic activity.

Human Dofetilide Binding

Human HERG transfected HEK293S cells were prepared and grown in-house. The collected cells were suspended in 50 mM Tris-HCl (pH 7.4 at 4° C.) and homogenized using a hand held Polytron PT 1200 disruptor set at full power for 20 sec on ice. The homogenates were centrifuged at 48,000×g at 4° C. for 20 min. The pellets were then resuspended, homogenized, and centrifuged once more in the same manner. The final pellets were resuspended in an appropriate volume of 50 mM Tris-HCl, 10 mM KCl, 1 mM $MgCl_2$ (pH 7.4 at 4° C.), homogenized, aliquoted and stored at −80° C. until use. An aliquot of membrane fractions was used for protein concentration determination using BCA protein assay kit (PIERCE) and ARVOsx plate reader (Wallac).

Binding assays were conducted in a total volume of 200 µl in 96-well plates. Twenty µl of test compounds were incubated with 20 µl of [$^3$H]-dofetilide (Amersham, final 5 nM) and 160 µl of membrane homogenate (25 µg protein) for 60 minutes at room temperature. Nonspecific binding was determined by 10 µM dofetilide at the final concentration. Incubation was terminated by rapid vacuum filtration over 0.5% presoaked GF/B Betaplate filter using Skatron cell harvester with 50 mM Tris-HCl, 10 mM KCl, 1 mM $MgCl_2$, pH 7.4 at 4° C. The filters were dried, put into sample bags and filled with Betaplate Scint. Radioactivity bound to filter was counted with Wallac Betaplate counter.

$I_{HERG}$ Assay

HEK 293 cells which stably express the HERG potassium channel were used for electrophysiological study. The methodology for stable transfection of this channel in HEK cells can be found elsewhere (Z. Zhou et al., 1998, Biophysical journal, 74, pp 230-241). Before the day of experimentation, the cells were harvested from culture flasks and plated onto glass coverslips in a standard MEM medium with 10% FCS. The plated cells were stored in an incubator at 37° C. maintained in an atmosphere of 95% $O_2$/5% $CO_2$. Cells were studied between 15-28 hrs after harvest.

HERG currents were studied using standard patch clamp techniques in the whole-cell mode. During the experiment the cells were superfused with a standard external solution of the following composition (mM); NaCl, 130; KCl, 4; $CaCl_2$, 2; $MgCl_2$, 1; Glucose, 10; HEPES, 5; pH 7.4 with NaOH. Whole-cell recordings was made using a patch clamp amplifier and patch pipettes which have a resistance of 1-3 MOhm when filled with the standard internal solution of the following composition (mM); KCl, 130; MgATP, 5; $MgCl_2$, 1.0; HEPES, 10; EGTA 5, pH 7.2 with KOH. Only those cells with access resistances below 15 MΩ and seal resistances>1 GΩ was accepted for further experimentation. Series resistance compensation was applied up to a maximum of 80%. No leak subtraction was done. However, acceptable access resistance depended on the size of the recorded currents and the level of series resistance compensation that can safely be used. Following the achievement of whole cell configuration and sufficient for cell dialysis with pipette solution (>5 min), a standard voltage protocol was applied to the cell to evoke membrane currents. The voltage protocol is as follows. The membrane was depolarized from a holding potential of −80 mV to +20 mV for 1000 ms. This was followed by a descending voltage ramp (rate 0.5 mV msec$^{-1}$) back to the holding potential. The voltage protocol was applied to a cell continuously throughout the experiment every 4 seconds (0.25 Hz). The amplitude of the peak current elicited around −40 mV during the ramp was measured. Once stable evoked current responses were obtained in the external solution, vehicle (0.5% DMSO in the standard external solution) was applied for 10-20 min by a peristalic pump. Provided there were minimal changes in the amplitude of the evoked current response in the vehicle control condition, the test compound of either 0.3, 1, 3, 10 μM was applied for a 10 min period. The 10 min period included the time which supplying solution was passing through the tube from solution reservoir to the recording chamber via the pump. Exposing time of cells to the compound solution was more than 5 min after the drug concentration in the chamber well reached the attempting concentration. There reversibility. Finally, the cells was exposed to high dose of dofetilide (5 μM), a specific IKr blocker, to evaluate the insensitive endogenous current.

All experiments were performed at room temperature (23±1° C.). Evoked membrane currents were recorded on-line on a computer, filtered at 500-1 KHz (Bessel −3 dB) and sampled at 1-2 KHz using the patch clamp amplifier and a specific data analyzing software. Peak current amplitude, which occurred at around −40 mV, was measured off line on the computer.

The arithmetic mean of the ten values of amplitude was calculated under control conditions and in the presence of drug. Percent decrease of $I_N$ in each experiment was obtained by the normalized current value using the following formula: $I_N=(1-I_D/I_C)\times 100$, where $I_D$ is the mean current value in the presence of drug and $I_C$ is the mean current value under control conditions. Separate experiments were performed for each drug concentration or time-matched control, and arithmetic mean in each experiment is defined as the result of the study.

Half-Life in Human Liver Microsomes (HLM)

Test compounds (1 μM) were incubated with 3.3 mM $MgCl_2$ and 0.78 mg/mL HLM (HL101) in 100 mM potassium phosphate buffer (pH 7.4) at 37° C. on the 96-deep well plate. The reaction mixture was split into two groups, a non-P450 and a P450 group. NADPH was only added to the reaction mixture of the P450 group. An aliquot of samples of P450 group was collected at 0, 10, 30, and 60 min time point, where 0 min time point indicated the time when NADPH was added into the reaction mixture of P450 group. An aliquot of samples of non-P450 group was collected at −10 and 65 min time point. Collected aliquots were extracted with acetonitrile solution containing an internal standard. The precipitated protein was spun down in centrifuge (2000 rpm, 15 min). The compound concentration in supernatant was measured by LC/MS/MS system.

The half-life value was obtained by plotting the natural logarithm of the peak area ratio of compounds/internal standard versus time. The slope of the line of best fit through the points yields the rate of metabolism (k). This was converted to a half-life value using following equations:

$$\text{Half-life} = \ln 2/k$$

Method of Gastric Emptying Model in Rats:

The effects of compounds on gastric emptying in rats were examined by the modified method of D. A. Droppleman et al. (J. Pharmacol. Methods 4, 227-230 (1980)). The test meal, non-fat caloric meal, was prepared according to the method of S. Ueki et al Arzneim.-Forsch./Drug Res. 49 (II), 618-625 (1999)). IGS-SD rats (Male, 7w, 230-270 g) were purchased from Charles River Japan (Atsugi). These rats were used in the experiments after one week acclimatization. In the experiments, rats were fasted 15 hrs before the experiments but allowed free access to water. Forty-five minutes prior to the start of the experiment, water was removed from the cage to prevent rats from taking water. Five minutes before the test meal administration, test compounds, cisapride or vehicle were dosed via an appropriate route to rats (n=8-10) in a volume of 0.1 ml per 100 g body weight. Cisapride (3 mg/kg) was used as a positive control for the experiment. Rats were given 3 ml of the test meal by gavage and were returned to the cages. Thirty minutes after the meal administration, rats were culled by $CO_2$ exposure. Following a midline laparotomy, the stomach is ligated at the lower esophageal sphincter (LES) and pylorus. Then the stomach was removed and weighed (A). After the stomach was opened and rinsed with 0.9% saline, it was blotted the face with the tissue to remove any excess liquid and weighed again (B). After avoiding the rats that had eaten feces or given artificial miss, gastric emptying rate for individual animals was calculated by the formula:

$$GE \text{ rate}(\%) = (A-B)/\text{weight of the test meal}.$$

Gastric Motility in Conscious Dogs:

The surgical operation in dogs was performed by the modified method of Z. Itoh et al. (Gastroenterol. Jpn., 12, 275-283 (1977)). The effects of test compounds on gastric motility in dogs were examined by the modified method of N. Toshida et al. (J. Pharmacol. Exp/Ther., 257, 781-787 (1991)).

An evaluation in the fasted state: Animals were chronically implanted with a strain gauge force transducer on the gastric body, and fasted overnight prior to the experiment. The gastric motility was continuously recorded by a telemetry system for 8 h after administration of the compound. To quantitate the change in gastrointestinal motility, the motor index was determined as the area under the contraction curves during each 2 h period divided by the peak height of interdigestive migrating contraction.

An evaluation in the postprandial state: Animals were chronically implanted with a strain gauge force transducer on the gastric body, and fasted overnight prior to the experiment. Postprandial motility was induced by feeding with solid meal (100 grams), and the compound was administered 2 h later. The gastric motility was continuously recorded by a telemetry system for 8 h after administration of the compound. The motor index was determined to quantitate the change in gastrointestinal motility as the area under the contraction curves during each 1 h period divided by the area under the contraction curves for 1 h before the compound administration.

The compounds of formula (I) of this invention can be administered via either the oral, parenteral or topical routes to mammals. In general, these compounds are most desirably administered to humans in doses ranging from 0.3 mg to 750 mg per day, preferably from 10 mg to 500 mg per day, although variations will necessarily occur depending upon the weight and condition of the subject being treated, the disease state being treated and the particular route of administration chosen. However, for example, a dosage level that is in the range of from 0.06 mg to 2 mg per kg of body weight per day is most desirably employed for treatment of inflammation.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging 5% to 70% by weight, preferably 10% to 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

EXAMPLES

The invention is illustrated in the following non-limiting examples in which, unless stated otherwise: all operations were carried out at room or ambient temperature, that is, in the range of 18-25° C.; evaporation of solvent was carried out using a rotary evaporator under reduced pressure with a bath temperature of up to 60° C.; reactions were monitored by thin layer chromatography (tlc) and reaction times are given for illustration only; melting points (m.p.) given are uncorrected (polymorphism may result in different melting points); the structure and purity of all isolated compounds were assured by at least one of the following techniques: tlc (Merck silica gel 60 $F_{254}$ precoated TLC plates or Merck $NH_2$ $F_{254}$, precoated HPTLC plates), mass spectrometry, nuclear magnetic resonance (NMR), infrared red absorption spectra (IR), microanalysis or powder X-ray diffraction (PXRD) pattern. Yields are given for illustrative purposes only. Flash column chromatography was carried out using Merck silica gel 60 (230-400 mesh ASTM) or Fuji Silysia Chromatorex® DU3050 (Amino Type, 30~50 µm). Low-resolution mass spectral data (EI) were obtained on a Integrity (Waters) mass spectrometer or a Automass 120 (JEOL) mass spectrometer. Low-resolution mass spectral data (ESI) were obtained on a ZMD2 (Waters) mass spectrometer or a Quattro II (Micromass) mass spectrometer. NMR data was determined at 270 MHz (JEOL JNM-LA 270 spectrometer) or 300 MHz (JEOL JNM-LA300) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br.=broad, etc. IR spectra were measured by a Shimazu infrared spectrometer (IR-470). Optical rotations were measured using a JASCO DIP-370 Digital Polarimeter (Japan Spectroscopic CO, Ltd.). PXRD pattern was determined using a Rigaku RINT-TTR powder X-ray diffractometer fitted with an automatic sample changer, a 2 theta-theta goniometer, beam divergence slits, a secondary monochromator and a scintillation counter. The sample was prepared for analysis by packing the powder on to an aluminum sample holder. The specimen was rotated by 60.00 rpm and scanned by 4°/min. Chemical symbols have their usual meanings; b.p. (boiling point), m.p. (melting point), l (liter(s)), ml (milliliter(s)), g (gram(s)), mg (milligram(s)), mol (moles), mmol (millimoles), eq. (equivalent(s)).

Example 1

N-({1-[(4-Hydroxytetrahydro-2H-pyran-4-yl)methyl]piperidin-4-yl}methyl)-3-isopropyl-2-oxo-2,3-dihydro-1H-benzimidazole-1-carboxamide hydrochloride

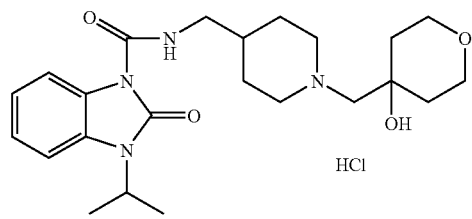

Step 1. tert-Butyl({1-[(4-hydroxytetrahydro-2H-pyran-4-yl)methyl]piperidin-4-yl}methyl)carbamate

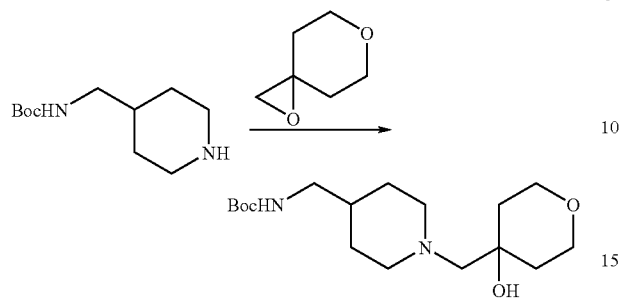

To a stirred solution of tert-butyl(piperidin-4-ylmethyl)carbamate (22.3 g, 104 mmol) in methanol was added 1,6-dioxaspiro[2.5]octane (14.2 g, 124 mmol, Satyamurthy, Nagichettiar et al., *Phosphorus Sulfur*, 1984, 19, 113) at ambient temperature.

Then, the mixture was heated at 60° C. for 4 h. The volatile components were removed by evaporation and the resulting viscous oil was precipitated with a mixture of hexane and diethylether. The precipitate was collected by filtration and recrystallized with a mixture of hexane and 2-propanol to give title compound 14.2 g (42%) as a colorless powder.

MS (ESI) m/z: 329 (M+H$^+$).

m.p.: 104° C.

$^1$H-NMR (CDCl$_3$) δ: 1.23-1.31 (2H, m), 1.44 (9H, s), 1.51-1.69 (8H, m), 2.27-2.38 (4H, m), 2.83-2.88 (2H, m), 3.00 (2H, t, J=6.2 Hz), 3.70-3.85 (4H, m). Anal. Calcd. for C$_{17}$H$_{32}$N$_2$O$_4$: C, 62.17; H, 9.82; N, 8.53. Found: C, 62.07; H, 9.92; N, 8.58.

Step 2. 4-{[4-(Aminomethyl)piperidin-1-yl]methyl}tetrahydro-2H-pyran-4-ol

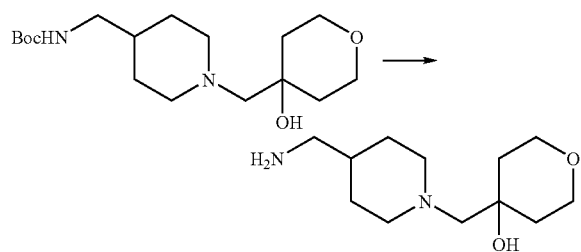

To a solution of tert-butyl({1-[(4-hydroxytetrahydro-2H-pyran-4-yl)methyl]piperidin-4-yl}methyl)carbamate (50.28 g, 153 mmol) in methanol was added 4N HCl in dioxane (200 mL, 800 mmol) at room temperature. After 4 h, the volatile materials were removed by evaporation. The resulting amorphous was precipitated with diethyl ether/methanol (5:1). The precipitate was collected and added to the ice cooled 6N NaOH aq. (200 mL) gradually. The mixture was extracted with dichloromethane/methanol (10:1) for 4 times. The combined organic phase was washed with brine, dried over MgSO$_4$ and concentrated to give 24.90 g (99%) of the title compound as pale brown amorphous.

MS (ESI) m/z: 229 (M+H$^+$).

$^1$H-NMR (CDCl$_3$) δ: 1.19-1.28 (2H, m), 1.44-1.63 (8H, m), 1.65-1.71 (2H, m), 2.32 (2H, s), 2.35 (2H, t, J=11.0 Hz), 2.57 (2H, d, J=5.7 Hz), 2.85-2.90 (2H, m), 3.70-3.81 (4H, m).

Step 3. N-({1-[(4-Hydroxytetrahydro-2H-pyran-4-yl)methyl]piperidin-4-yl}methyl)-3-isopropyl-2-oxo-2,3-dihydro-1H-benzimidazole-1-carboxamide

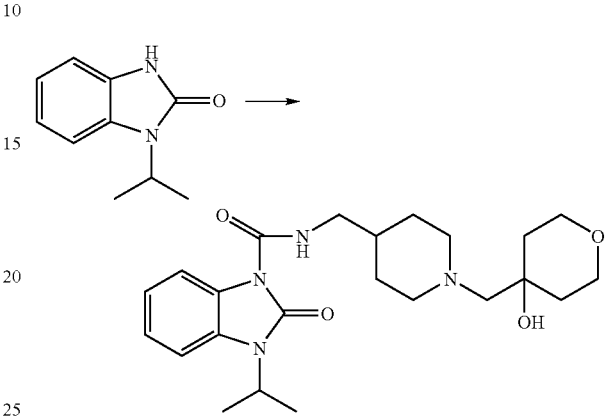

To a stirred mixture of 1-isopropyl-1,3-dihydro-2H-benzimidazol-2-one (*J. Med. Chem*. 1999, 42, 2870-2880) (23.0 g, 130 mmol) and triethylamine (54.6 mL, 392 mmol) in tetrahydrofuran (300 mL) was added triphosgen (38.8 g, 130 mmol) in tetrahydrofuran (200 mL) gradually at room temperature. Then, the mixture was heated at 80° C. for 4 h. After cooling, a solution of 4-{[4-(aminomethyl)piperidin-1-yl]methyl}tetrahydro-2H-pyran-4-ol (step 2 of Example 1) (24.9 g, 109 mmol) and triethylamine (45 mL, 109 mmol) in tetrahydrofuran (500 mL) was added to the mixture. Then, the mixture was heated at 80° C. for 6 h. After cooling, sat. NaHCO$_3$ aq was added to the mixture. The mixture was extracted with ethyl acetate (500 mL×4). The extracts were washed with brine, dried over MgSO$_4$ and concentrated. The residue was chromatographed on a column of aminopropyl-silica gel eluting with hexane/ethyl acetate (3:1) to give 31.3 g (67%) of the title compound as a white solid.

$^1$H NMR (DMSO-d$_6$) δ 8.80 (1H, br t, J=6.0 Hz), 8.06 (1H, m), 7.41 (1H, m), 7.19 (1H, dt, J=1.5, 7.7 Hz), 7.12 (1H, dt, J=1.3, 7.7 Hz), 4.64 (1H, septet, J=7.0 Hz), 4.08 (1H, br s), 3.68-3.44 (4H, m), 3.19 (2H, t, J=6.0 Hz), 2.89 (2H, m), 2.20 (2H, br s), 2.09 (2H, m), 1.68-1.10 (9H, m), 1.47 (6H, d, J=7.0 Hz).

MS (ESI) m/z: 431 (M+H$^+$).

Anal. Calcd. for C$_{23}$H$_{34}$N$_4$O$_4$: C, 64.16; H, 7.96; N, 13.01. Found: C, 64.13; H, 7.97; N, 12.99.

Step 4. N-({1-[(4-Hydroxytetrahydro-2H-pyran-4-yl)methyl]piperidin-4-yl}methyl)-3-isopropyl-2-oxo-2,3-dihydro-1H-benzimidazole-1-carboxamide hydrochloride To a stirred solution of N-({1-[(4-hydroxytetrahydro-2H-pyran-4-yl)methyl]piperidin-4-yl}methyl)-3-isopropyl-2-oxo-2,3-dihydro-1H-benzimidazole-1-carboxamide (27.0 g, 62 mmol) in methanol (150 mL) was added 10% HCl-methanol (100 mL) at ambient temperature. After 30 min, the volatile materials were removed by evaporation. The resulting amorphous was precipitated by ethanol/diethylether. The precipitate was recrystallized from ethanol/diethylether (1:1) to give 26.5 g (90%) of title compound as a colorless powder.

$^1$H-NMR (DMSO-d$_6$) δ: 1.49 (6H, d, J=6.9 Hz), 1.50-1.70 (4H, m), 1.76-1.91 (5H, m), 3.00-3.12 (3H, m), 3.15-3.45 (3H, m), 3.60-3.70 (6H, m), 4.61-4.69 (1H, m), 5.46-5.49 (1H, m), 7.13 (1H, t, J=7.8 Hz) 7.20 (1H, t, J=7.8 Hz), 7.42 (1H, d, J=7.9 Hz), 8.07 (1H, d, J=8.0 Hz), 8.86 (1H, m), 9.61-9.81 (1H, m)

MS (ESI) m/z: 431 (M+H$^+$).

Anal. Calcd. for C23H35N4O4Cl: C, 59.15; H, 7.55; N, 2.00. Found: C, 58.81; H, 7.57; N, 11.85.

Alternative route to synthesize 4-{[4-(aminomethyl)piperidin-1-yl]methyl}tetrahydro-2H-pyran-4-ol is described below.

Step 1. Benzyl({1-[(4-hydroxytetrahydro-2H-pyran-4-yl)methyl]piperidin-4-yl}methyl)carbamate

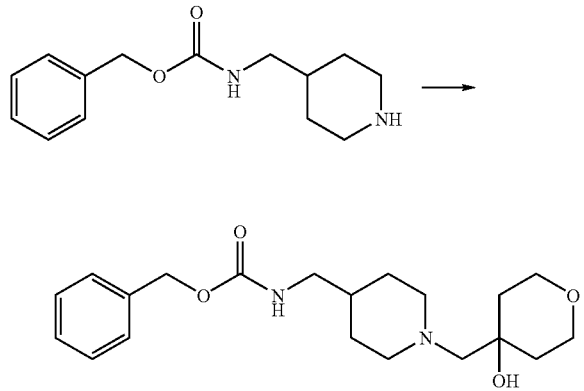

A mixture of benzyl(piperidin-4-ylmethyl)carbamate (7.77 g, 31.3 mmol, Bose, D. Subhas et al., *Tetrahedron Lett.*, 1990, 31, 6903) and 1,6-dioxaspiro[2.5]octane (4.29 g, 37.6 mmol, Satyamurthy, Nagichettiar et al., *Phosphorus Sulfur*, 1984, 19, 113) in methanol (93 mL) was stirred at room temperature for 20 h. Then the mixture was refluxed for 8 h. After cooling to room temperature, the solvent was removed in vacuo. The residue was chromatographed on a column of silica gel eluting with methanol/dichloromethane (1:20) to give 5.60 g (49%) of the title compound as a colorless oil.

Step 2. 4-{[4-(Aminomethyl)piperidin-1-yl]methyl}tetrahydro-2H-pyran-4-ol

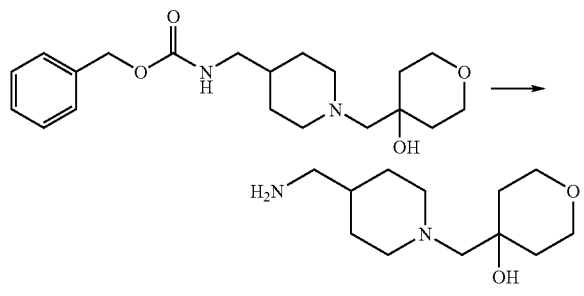

A mixture of benzyl({1-[(4-hydroxytetrahydro-2H-pyran-4-yl)methyl]piperidin-4-yl}methyl)carbamate (5.60 g, 15.5 mmol, step 1) and palladium on activated carbon (10 wt. %, 1.20 g) in methanol (250 mL) was hydrogenated at room temperature for 20 h. Then, the mixture was filtered through a pad of Celite, and the filtrate was concentrated in vacuo to give 3.30 g (94%) of the title compound as slightly yellow oil.

Following is an another route to synthesize 4-{[4-(aminomethyl)piperidin-1-yl]methyl}tetrahydro-2H-pyran-4-ol.

Step 1. 1-[(4-hydroxytetrahydro-2H-pyran-4-yl)methyl]piperidine-4-carboxamide

The mixture of trimethylsulfoxonium iodide (0.791 g, 3.52 mmol) and 2N—NaOH aq (1.76 mL, 3.52 mmol) in acetonitrile (1.62 mL) was stirred at 50° C. for 30 min. Then to the mixture was added tetrahydro-4H-pyran-4-one (0.324 g, 3.20 mmol) and the resulting mixture was stirred at 50° C. for 3 h. Sat. NaCl aq. (10 mL) was added to the reaction mixture at room temperature and organic layer was extracted with CH$_2$Cl$_2$ (20 mL), dried over Na$_2$SO$_4$, filtered and concentrated.

After removal of the solvent, MeOH (1.62 mL) and isonipecotamide (0.381 g, 2.88 mmol) were added to the residue, the mixture was stirred at 75° C. for 14 h under N$_2$. The reaction mixture was concentrated and the residue was recrystallized from MeOH-acetonitrile to give 0.484 g (2.00 mmol) of title compound as a white solid.

$^1$H-NMR (300 MHz, DMSO-d$_6$) δ 7.19 (br s, 1H), 6.69 (br s, 1H), 4.10 (s, 1H), 3.70-3.50 (m, 4H), 2.95-2.85 (m, 2H), 2.20 (s, 2H), 2.15-1.85 (m, 3H), 1.65-1.50 (m, 6H), 1.40-1.25 (m, 2H).

Step 2. 4-{[4-(Aminomethyl)piperidin-1-yl]methyl}tetrahydro-2H-pyran-4-ol tosylate To a stirred suspension of NaBH$_4$ (0.505 g, 13.2 g) in triethylene glycol dimethyl ether (12.8 mL) was added the solution 1-[(4-hydroxytetrahydro-2H-pyran-4-yl)methyl]piperidine-4-carboxamide (0.640 g, 2.64 mmol) and AcOH (0.765 mL, 13.2 mmol) in triethylene glycol dimethyl ether (3.2 mL) dropwise at 80° C. under N$_2$. The reaction mixture was quenched with 2N—HCl aq until pH value was <3, then the resulting mixture was stirred at room temperature for 1 h. To the mixture CH$_2$Cl$_2$ (30 mL) and 2N—NaOH aq. was added until pH value of aqueous layer was >10. Organic layer was extracted with CH$_2$Cl$_2$ for three times, and the combined organic layer was dried over Na$_2$SO$_4$, filtered and concentrated.

To the residual solution (title compound in triethylene glycol dimethyl ether) the solution of p-toluenesulfonic acid monohydrate (0.408 g, 2.11 mmol) in MeOH (1.28 mL) was added at 60° C., then the mixture was cooled to room temperature. Appeared solids were collected by suction and wash with hexane to give title compound (0.340 g, 0.849 mmol) as a white solid.

$^1$H-NMR (300 MHz, DMSO-d$_6$) δ 7.61 (br s, 2H), 7.55-7.40 (m, 2H), 7.15-7.05 (m, 2H), 4.11 (br s, 1H), 3.70-3.45 (m, 4H), 2.95-2.85 (m, 2H), 2.68 (d, J=7.0, 2H), 2.29 (s, 3H), 2.22 (s, 2H), 2.07 (t, J=11.0, 2H), 1.65-1.45 (m, 4H), 1.55-1.35 (m, 1H), 1.40-1.25 (m, 2H), 1.30-1.10 (m, 2H).

Example 2

N-({1-[(4-Hydroxytetrahydro-2H-pyran-4-yl)methyl]piperidin-4-yl}methyl)-3-isopropyl-2-oxo-2,3-dihydro-1H-benzimidazole-1-carboxamide Hemiedisylate

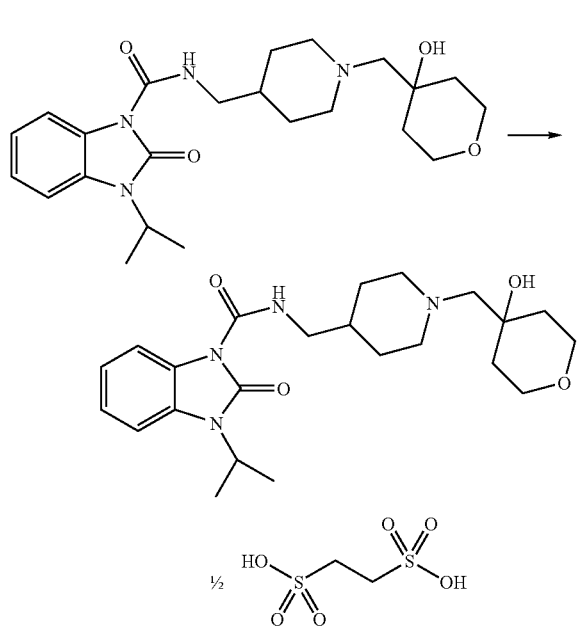

To a stirred solution of N-({1-[(4-hydroxytetrahydro-2H-pyran-4-yl)methy]piperidin-4-yl}methyl)-3-isopropyl-2-oxo-2,3-dihydro-1H-benzimidazole-1-carboxamide 1.51 g (3.51 mmol) in ethyl acetate (10 mL) and methanol (10 mL) was added a solution of 1,2-ethanedisulfonic acid dihydrate 397 mg (1.75 mmol) in methanol (5.0 mL) and the resulting suspension was stirred for 5 h at room temperatute. The mixture was filtered and the first crop was dried under vacuum for 5 h at 100° C. to give 1.78 g of crude product. 1.61 g of the crude product was dissolved in methanol (20 mL) and ethyl acetate (20 mL) was added to the solution. The resulting suspension was stirred for 2 h at room temperatute. The mixture was filtered and the crop was dried under vacuum for 4 h at 100° C. to give the titled compound 1.13 g (61%) as colorless crystals.

MS (ESI) m/z: 431 (M+H)$^+$.

m.p.: 233° C.

IR (KBr) v: 2866, 1738, 1683, 1558, 1373, 1217, 1028, 756 cm$^{-1}$.

$^1$H NMR (DMSO-d$_6$) δ 8.96 (0.25H, br s), 8.85 (1H, br t, J=6.0 Hz), 8.61 (0.75H, br s), 8.06 (1H, m), 7.43 (1H, m), 7.21 (1H, dt, J=1.3, 7.7 Hz), 7.13 (1H, dt, J=1.2, 7.7 Hz), 5.26 (1H, br s), 4.65 (1H, septet, J=7.0 Hz), 3.74-2.92 (12H, m), 2.64 (2H, s), 2.00-1.35 (9H, m), 1.47 (6H, d, J=7.0 Hz).

Anal. calcd. for C$_{23}$H$_{34}$N$_4$O$_4$.0.5 C$_2$H$_6$O$_6$S$_2$: C, 54.84; H, 7.09; N, 10.66; S, 6.10.

Found: C, 54.50; H, 7.24; N, 10.60; S, 6.08.

PXRD pattern angle (2-Theta°): 10.2, 11.9, 16.3, 17.3, 17.6, 21.8, 24.2.

Example 3

3-Isopropyl-N-{[1-(2-morpholin-4-yl-2-oxoethyl)piperidin-4-yl]methyl}-2-oxo-2,3-dihydro-1H-benzimidazole-1-carboxamide Monooxalate

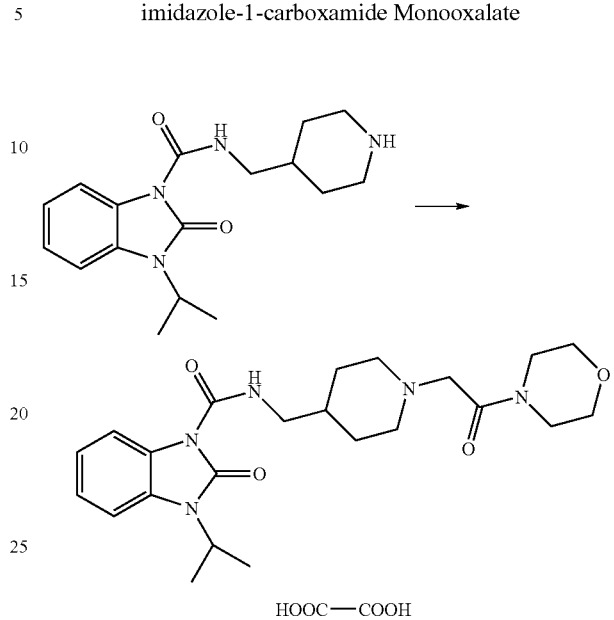

The tilted compound was prepared with the similar method shown in the Step 3 of Preperation 1 by using 4-(chloroacetyl)morpholine (B. G. Hazra; V. S. Pore; S. P. Maybhate, *Org. Prep. Proced. Int.*, 1989, 21, 355-8).

MS (ESI) m/z: 440 (M+H)$^+$.

m.p.: 194.2° C.

IR (KBr) v: 3443, 2934, 1765, 1728, 1686, 1659, 1612, 1551 cm$^{-1}$.

$^1$H-NMR (CDCl$_3$) (free base) δ: 9.00-8.88 (1H, m) 8.30-8.22 (1H, m), 7.23-7.12 (3H, m), 4.78-4.62 (1H, m), 3.66 (4H, s), 3.70-3.58 (4H, m), 3.32 (2H, t, J=6.3 Hz), 3.15 (2H, s), 2.94-2.84 (2H, m), 2.14-2.01 (2H, m), 1.86-1.23 (5H, m), 1.56 (6H, d, J=7.0 Hz).

$^1$H-NMR (DMSO-d$_6$) (salt form) δ: 8.92-8.80 (1H, m) 8.07 (1H, d, J=7.7 Hz), 7.45 (1H, d, J=7.5 Hz), 7.26-7.06 (2H, m), 4.76-4.56 (1H, m), 4.10-2.60 (18H, m), 1.90-1.40 (3H, m), 1.49 (6H, d, J=6.9 Hz).

Anal. Calcd. for C$_{25}$H$_{35}$N$_5$O$_8$: C, 56.27; H, 6.61; N, 13.13. Found: C, 56.25; H, 6.82; N, 12.98.

Example 4

3-Isopropyl-N-{[1-(3-morpholin-4-yl-3-oxopropyl)piperidin-4-yl]methyl}-2-oxo-2,3-dihydro-1H-benzimidazole-1-carboxamide Monooxalate

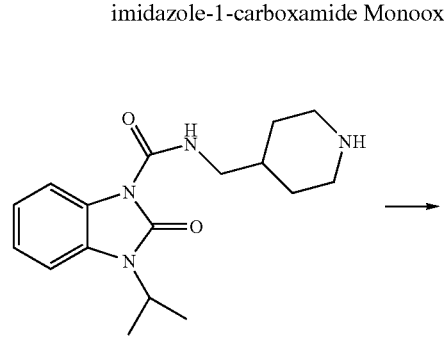

-continued

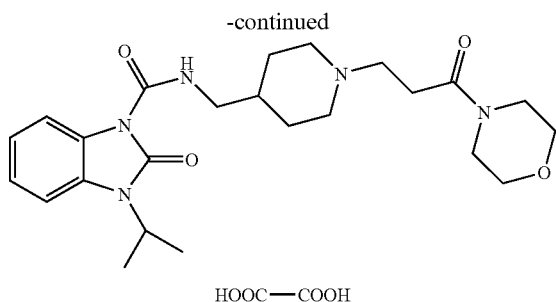

HOOC—COOH

A mixture of 3-isopropyl-2-oxo-N-(piperidin-4-ylmethyl)-2,3-dihydro-1H-benzimidazole-1-carboxamide (150 mg, 0.474 mmol) and 4-(3-chloro-propanoyl)-morpholine (G. Mattalia; C. Serafini; U. Bucciarelli, Fannaco, Ed. Sci., 1976, 31, 457-67) (300 mg, 1.185 mmol) in 4.7 ml N,N-dimethylformamide was added triethylamine (0.23 ml, 1.659 mmol) and sodium iodide (178 ml, 1.185 mmol). The reaction mixture was stirred at 90° C. for 6 days. The reaction mixture was then concentrated by evaporation. The residue was diluted aqueous $NaHCO_3$ 10 ml, extracted with dichloromethane 30 ml for three times. The combined extract was dried over $MgSO_4$ and concentrated. Preparative TLC (elutent: $CH_2Cl_2$/methanol=10/1) afforded a brown amorphous oil 130 mg (60%). The amorphous (130 mg) was dissolved in 3 ml methanol and acidified with a solution of 24 mg oxalic acid in 2 ml MeOH. The mixture was concentrated. Crystallization of the resulting residue with AcOEt-EtOH afforded a white amorphous 107 mg as the titled compound.

MS (ESI) m/z: 458 (M+H)⁺.

IR (KBr) ν: 3443, 2941, 1732, 1697, 1686, 1647, 1638, 1558 cm⁻¹.

¹H-NMR (CDCl₃) (free base) δ: 9.06-8.94 (1H, br) 8.24-8.19 (1H, m), 7.26-7.10 (3H, m), 4.76-4.64 (1H, m), 3.75-2.80 (10H, m), 2.60-1.30 (13H, m), 1.56 (6H, d, J=7.0 Hz).

¹H-NMR (CDCl₃) (salt form) δ: 9.10-9.00 (1H, m) 8.27-8.17 (1H, m), 7.33-7.12 (3H, m), 4.87-4.62 (1H, m), 3.78-2.65 (16H, m), 2.20-1.60 (7H, m), 1.56 (6H, d, J=6.9 Hz).

Anal. Calcd. for $C_{26}H_{37}N_5O_8 \cdot 0.9C_2H_2O_4 \cdot 1.3H_2O$: C, 51.21; H, 6.40; N, 10.74.

Found: C, 50.90; H, 6.26; N, 11.13.

Example 5

3-Isopropyl-N-{[1-(4-morpholin-4-yl-4-oxobutyl)piperidin-4-yl]methyl}-2-oxo-2,3-dihydro-1H-benzimidazole-1-carboxamide monooxalate

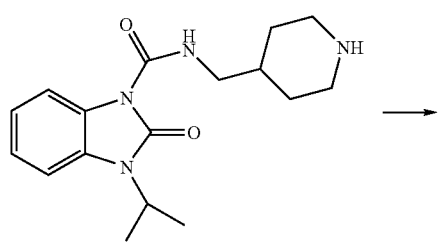

-continued

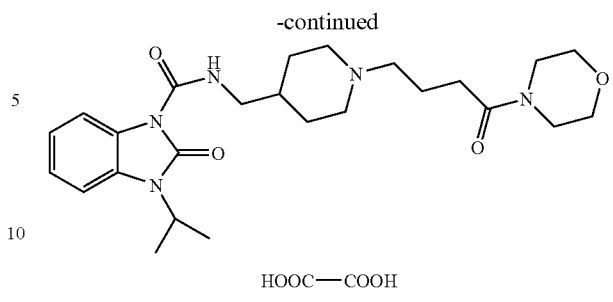

HOOC—COOH

The tilted compound was prepared with the similar method shown in the example 4 by using 4-(4-chloro-butyryl)-morpholine (Schlesinger; Prill; B. G. Hazra; *J. Amer. Chem. Soc.*, 1956, 78, 6123-6124).

MS (ESI) m/z: 472 (M+H)⁺.

IR (KBr) ν: 3443, 1728, 1686, 1647-1616, 1551 cm⁻¹.

¹H-NMR (CDCl₃) (free base) δ: 9.02-8.88 (1H, m) 8.31-8.20 (1H, m), 7.22-7.04 (3H, m), 4.80-4.60 (1H, m), 3.66-3.56 (8H, m), 3.40-3.22 (2H, m), 3.00-2.88 (2H, m), 2.50-2.30 (6H, m), 2.00-1.20 (7H, m), 1.57 (6H, d, J=7.1 Hz).

¹H-NMR (DMSO-d₆) (salt form) δ: 8.93-8.79 (1H, m) 8.07 (1H, d, J=7.5 Hz), 7.44 (1H, d, J=7.5 Hz), 7.27-7.08 (2H, m), 4.75-4.58 (1H, m), 4.47-2.30 (18H, m), 1.90-0.90 (7H, m), 1.49 (6H, d, J=6.9 Hz).

Anal. Calcd. for $C_{27}H_{39}N_5O_8$: C, 57.74; H, 7.00; N, 12.47. Found: C, 57.52; H, 7.03; N, 12.32.

Example 6

N-({1-[(trans-1,4-Dihydroxyhexyl)methyl]piperidin-4-yl}methyl)-3-isopropyl-2-oxo-2,3-dihydro-1H-benzimidazole-1-carboxamide Hydrochloride

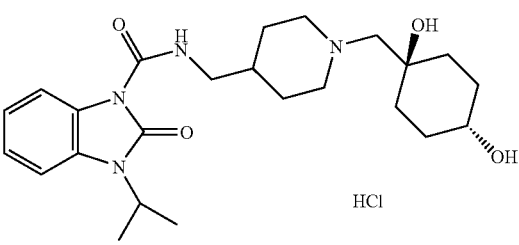

HCl

Step 1. tert-Butyl(1-oxaspiro[2,5]oct-6-yloxy)diphenylsilane

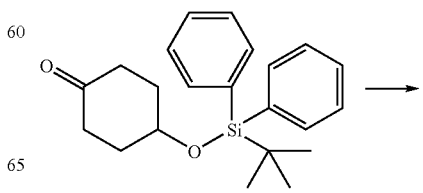

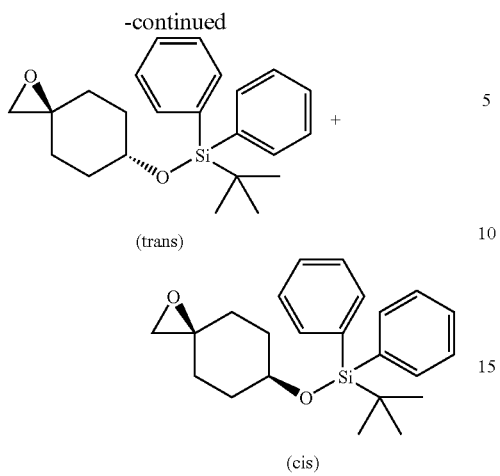

(trans)

(cis)

To a stirred suspension of sodium hydride (60% in mineral oil, 441 mg, 11.0 mmol) in DMSO (7 ml) was added trimethylsulfoxonium iodide (2.53 g, 11.5 mmol) at room temperature, and the mixture was stirred at room temperature for 30 min. To this mixture was added a solution of 4-{[tert-butyl (diphenyl)silyl]oxy}cyclohexanone (Okamura, William H. et al., *J. Org. Chem.*, 1993, 58, 600-610, 3.53 g, 10.0 mmol) in DMSO (35 ml) dropwise at room temperature, the mixture was stirred at room temperature for 2 h. Then the mixture was diluted with water (600 ml), and extracted with diethylether (200 ml×4). The combined organic layer was dried over magnesium sulfate, and concentrated in vacuo. The residue was chromatographed on a column of silica gel eluting with n-hexane/ethyl acetate (1:10), and then purified with PTLC eluting with n-hexane/ethyl acetate (1:15) to give 459 mg (13%, trans) and 390 mg (11%, cis) of the title compound as colorless oil respectively.

(trans)

$^1$H-NMR (CDCl$_3$) δ: 7.70-7.66 (4H, m), 7.46-7.35 (6H, m), 4.03-3.97 (1H, m), 2.63 (2H, s), 2.07-1.63 (8H, m), 1.08 (9H, s).

(cis)

$^1$H-NMR (CDCl$_3$) δ: 7.70-7.65 (4H, m), 7.46-7.35 (6H, m), 3.97-3.83 (1H, m), 2.58 (2H, s), 1.83-1.37 (8H, m), 1.07 (9H, s).

Step 2. N-{[1-({trans-4-[tert-Butyl(diphenyl)silyl] oxy-1-hydroxycyclohexyl}methyl)piperidin-4-yl] methyl}-3-isopropyl-2-oxo-2,3-dihydro-1H-benzimidazole-1-carboxamide

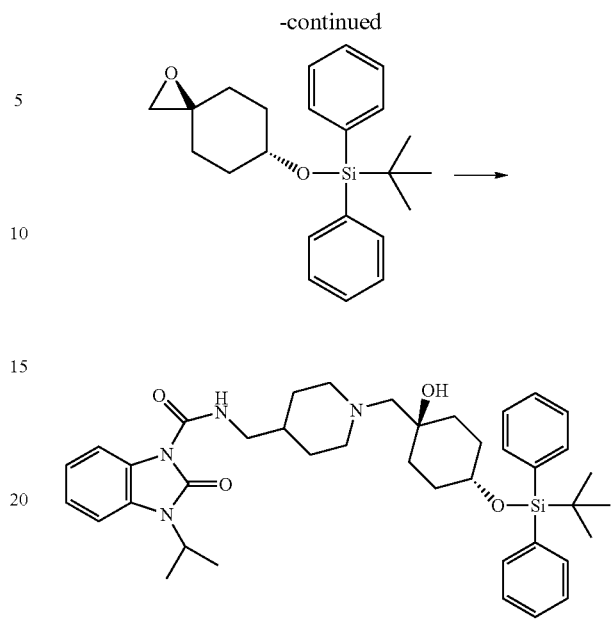

A mixture of tert-butyl[(3R,6R)-1-oxaspiro[2.5]oct-6-yloxy]diphenylsilane (Step 1, trans-isomer, 283.0 mg, 0.772 mmol) and 3-isopropyl-2-oxo-N-(piperidin-4-ylmethyl)-2,3-dihydro-1H-benzimidazole-1-carboxamide (Preperation 1, step 2, 2.48 g, 0.0194 mol) in MeOH (4 ml) was heated at 50° C. with stirring for 2 days. After cooling, the reaction mixture was evaporated to remove the solvent, and residue was chromatographed on a column of silica gel eluting with ethyl acetate 1n-hexane (1:10) then methanol/dichloromethane (1:20) to give 308.1 mg (58%) of the title compound as a colorless syrup.

MS (ESI) m/z: 683 (M+H)$^+$.

$^1$H-NMR (CDCl$_3$) δ: 8.93 (1H, m), 8.32-8.23 (1H, m), 7.72-7.60 (4H, m), 7.46-7.32 (6H, m), 7.22-7.10 (3H, m), 4.80-4.62 (1H, m), 3.96 (1H, m), 3.31 (2H, t, J=6.26 Hz), 2.92 (2H, d, J=10.88 Hz), 2.45-2.29 (4H, m), 1.85-1.65 (6H, m), 1.65-1.43 (9H, m, including 6H, d, J=7.09 Hz at 1.56 ppm), 1.43-1.25 (4H, m), 1.06 (9H, s).

Step 3. N-({1-[(trans-1,4-Dihydroxycyclohexyl)methyl]piperidin-4-yl}methyl)-3-isopropyl-2-oxo-2,3-dihydro-1H-benzimidazole-1-carboxamide hydrochloride

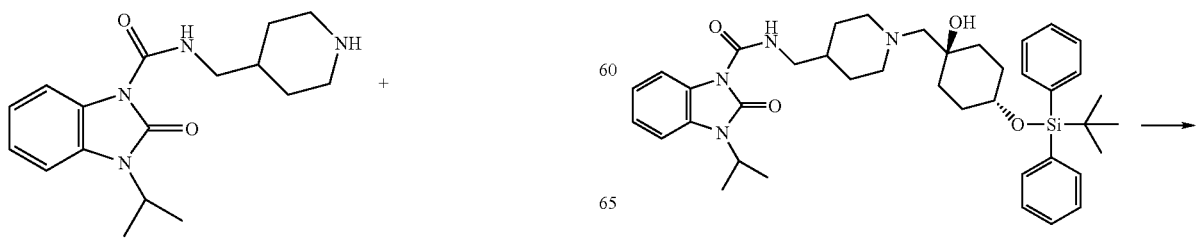

-continued

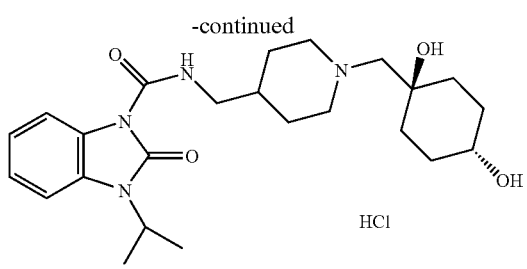

A mixture of tert-butyl N-{[1-({trans-4-[tert-butyl(diphenyl)silyl]oxy-1-hydroxycyclohexyl}methyl)piperidin-4-yl]methyl}-3-isopropyl-2-oxo-2,3-dihydro-1H-benzimidazole-1-carboxamide (234 mg, 0.343 mol) and HCl solution of MeOH (50 ml) was stirred at room temperature for 4 h. Then the solvent was removed in vacuo. The residue was basified with saturated aqueous NaHCO$_3$ (30 ml), extracted with CH$_2$Cl$_2$ (30 ml×3 times) and the combined organic layer was dried over Na$_2$SO$_4$. Removal of the solvent gave a residue, which was chromatographed on a column of NH-silica gel eluting with ethyl acetate/n-hexane (1:1-2:1) to give 140.1 mg (92%) of the title compound as a colorless syrup.

MS (ESI) m/z: 445 (M+H)$^+$.

$^1$H NMR (CDCl$_3$) δ: 8.93 (1H, br t, J=5.87 Hz), 8.32-8.20 (1H, m), 7.25-7.03 (3H, m), 4.80-4.62 (1H, m), 3.94 (1H, m), 3.31 (2H, t, J=6.10 Hz), 2.89 (2H, br d, J=11.53 Hz), 2.36 (2H, s), 2.34 (2H, t, J=11.86 Hz), 2.00-1.85 (2H, m), 1.82-1.25 (18H, m, including 6H, d, J=7.09 Hz at 1.56 ppm).

140.1 mg of this syrup was dissolved in HCl solution in MeOH (4 ml), concentrated, and dried in vacuo at 50° C. for 5 h to give 139.2 mg of title compound as a yellow amorphous solid.

MS (ESI) m/z: 445 (M+H)$^+$.

$^1$H NMR (DMSO-d$_6$) δ: 9.35-8.75 (1H, m), 8.86 (1H, t, J=6.59 Hz), 8.07 (1H, d, J=7.74 Hz), 7.44 (1H, d, J=7.58 Hz), 7.22 (1H, dt, J=1.15 Hz, 7.42 Hz), 7.14 (1H, dt, J=1.32 Hz, 7.74 Hz), 5.04 (1H, br s), 4.75-4.45 (1H, m), 3.70 (1H, br s), 3.59 (2H, d, J=11.70 Hz), 3.50-2.90 (8H, m), 1.90-1.57 (8H, m), 1.57-1.30 (10H, m, including 6H, d, J=6.92 Hz at 1.49 ppm)

IR(KBr): 3285, 2936, 2677, 1728, 1686, 1611, 1549, 1481, 1375, 1298, 1204, 1157, 1101, 1018, 762 cm$^{-1}$

Anal. Calcd for C$_{24}$H$_{36}$N$_4$O$_4$—HCl-2H$_2$O: C, 57.76; H, 7.88; N, 11.23. Found: C, 57.54; H, 7.90; N, 11.21.

PXRD pattern angle (2-Theta°): 8.3, 14.5, 17.7, 18.3, 19.1, 26.4, 27.5.

Example 7

N-({1-[(cis-1,4-Dihydroxyhexyl)methyl]piperidin-4-yl}methyl)-3-isopropyl-2-oxo-2,3-dihydro-1H-benzimidazole-1-carboxamide Hydrochloride

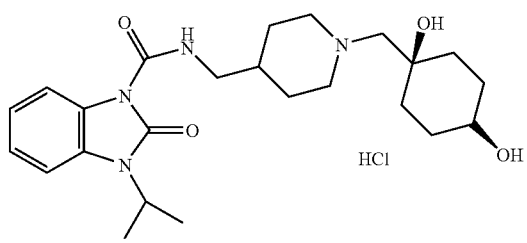

Step 1. N-{[1-({cis-4-[tert-Butyl(diphenyl)silyl]oxy-1-hydroxycyclohexyl}methyl)piperidin-4-yl]methyl}-3-isopropyl-2-oxo-2,3-dihydro-1H-benzimidazole-1-carboxamide

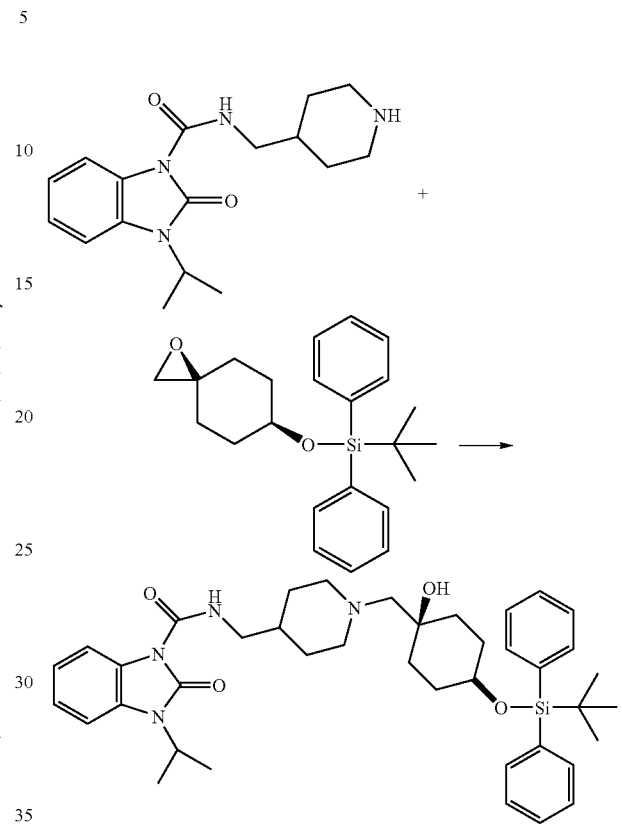

The title compound was prepared according to the procedure described of Step 2 in the Example 6 using tert-butyl [(3S,6S)-1-oxaspiro[2.5]oct-6-yloxy]diphenylsilane (Example 6, Step 1, cis-isomer, 311.0 mg, 0.848 mmol) instead of tert-butyl[(3R,6R)-1-oxaspiro[2.5]oct-6-yloxy]diphenylsilane.

MS (ESI) m/z: 683 (M+H)$^+$.

$^1$H-NMR (CDCl$_3$) δ: 8.91 (1H, t, J=5.87 Hz), 8.30-8.22 (1H, m), 7.72-7.63 (4H, m), 7.45-7.30 (6H, m), 7.20-7.10 (3H, m), 4.80-4.63 (1H, m), 3.59 (1H, m), 3.29 (2H, t, J=6.24 Hz), 2.83 (2H, d, J=11.74 Hz), 2.26 (2H, t, J=11.55 Hz), 2.18 (2H, s), 1.85-1.65 (4H, m), 1.65-1.50 (11H, m, including 6H, d, J=7.15 Hz at 1.56 ppm), 1.40-1.30 (2H, m), 1.15-1.00 (11H, m, including 9H, s, 1.05 ppm).

Step 2. N-({1-[(cis-1,4-Dihydroxycyclohexyl)methyl]piperidin-4-yl}methyl)-3-isopropyl-2-oxo-2,3-dihydro-1H-benzimidazole-1-carboxamide Hydrochloride

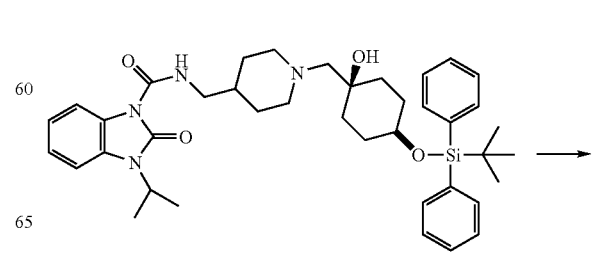

-continued

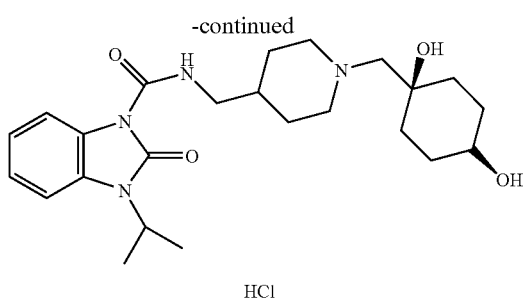

HCl

The title compound was prepared according to the procedure described of Step 3 in the Example 6 using N-{[1-({cis-4-[tert-butyl(diphenyl)silyl]oxy-1-hydroxycyclohexyl}methyl)piperidin-4-yl]methyl}-3-isopropyl-2-oxo-2,3-dihydro-1H-benzimidazole-1-carboxamide (295.0 mg, 0.432 mmol) instead of N-{[1-({trans-4-[diphenyl(trimethylsilyl)methoxy]-1-hydroxycyclohexyl}methyl)piperidin-4-yl]methyl}-3-isopropyl-2-oxo-2,3-dihydro-1H-benzimidazole-1-carboxamide.

MS (ESI) m/z: 445 (M+H)$^+$.

$^1$H NMR (CDCl$_3$) δ: 8.93 (1H, br t, J=5.60 Hz), 8.31-8.22 (1H, m), 7.25-7.10 (3H, m), 4.80-4.62 (1H, m), 3.63-3.49 (1H, m), 3.31 (2H, t, J=6.10 Hz), 2.89 (2H, br d, J=11.54 Hz), 2.33 (2H, dt, J=1.81 Hz, 11.70 Hz), 1.85-1.60 (16H, m, including 6H, d, J=7.09 Hz at 1.57 ppm), 1.45-1.18 (4H, m).

165.7 mg of this syrup was dissolved in HCl solution in MeOH (4 ml), concentrated, and dried in vacuo at 50° C. for 5 h to give 164.7 mg of title compound as a yellow amorphous solid.

MS (ESI) m/z: 445 (M+H)$^+$.

$^1$H NMR (DMSO-d$_6$) δ: 9.30-8.90 (1H, m), 8.86 (1H, t, J=5.93 Hz), 8.07 (1H, d, J=7.58 Hz), 7.44 (1H, d, J=7.58 Hz), 7.22 (1H, dt, J=1.48 Hz, 7.75 Hz), 7.15 (1H, dt, J=1.15 Hz, 7.74 Hz), 4.75-4.58 (1H, m), 3.70-2.90 (11H, m), 1.90-1.67 (6H, m), 1.67-1.20 (12H, m, including 6H, d, J=6.92 Hz at 1.49 ppm).

IR(KBr): 3294, 2936, 2673, 1728, 1686, 1611, 1545, 1479, 1375, 1298, 1203, 1158, 1134, 1101, 1051, 762 cm$^{-1}$

Anal. Calcd for C$_{24}$H$_{36}$N$_4$O$_4$—HCl-5H$_2$O: C, 54.79; H, 8.05; N, 10.65. Found: C, 54.75; H, 7.88; N, 10.56.

Example 8

6-Fluoro-N-({1-[(4-hydroxytetrahydro-2H-pyran-4-yl)methyl]piperidin-4-yl}methyl)-3-isopropyl-2-oxo-2,3-dihydro-1H-benzimidazole-1-carboxamide Hydrochloride

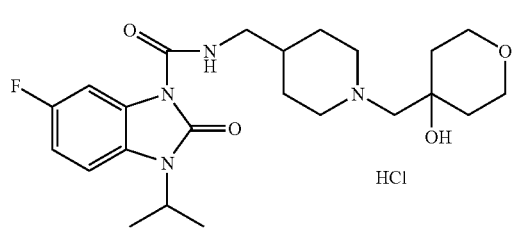

HCl

Step 1. 6-Fluoro-N-({1-[(4-hydroxytetrahydro-2H-pyran-4-yl)methyl]piperidin-4-yl}methyl)-3-isopropyl-2-oxo-2,3-dihydro-1H-benzimidazole-1-carboxamide

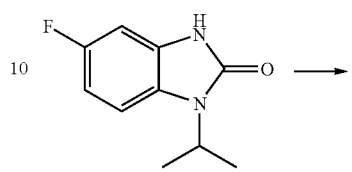

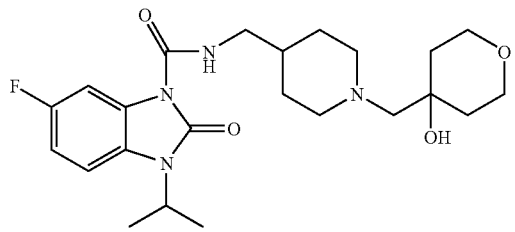

The title compound was prepared according to the procedure described in Step 3 of Example 1 from 5-fluoro-1-isopropyl-1,3-dihydro-2H-benzimidazol-2-one (I. Tapia et al., J. Med. Chem., 1999, 42, 2880.) and 4-{[4-(aminomethyl)piperidin-1-yl]methyl}tetrahydro-2H-pyran-4-ol (step 2 of Example 1).

MS (ESI) m/z: 449 (M+H$^+$).

$^1$H-NMR (CDCl$_3$) β: 1.12-1.70 (8H, m), 1.55 (6H, d, J=7.0 Hz), 1.74 (2H, brd, 12.8 Hz), 2.31 (2H, s), 2.35 (2H, brt, J=11.9 Hz), 2.88 (2H, brd, J=11.7 Hz), 3.30 (2H, t, J=6.2 Hz), 3.70-3.85 (4H, m), 4.62-4.75 (1H, m), 6.90 (1H, td, J=9.0, 2.4 Hz), 7.02-7.07 (1H, m), 8.05 (1H, dd, J=9.5, 2.6 Hz), 8.85-8.92 (1H, m).

Step 2. 6-Fluoro-N-({1-[(4-hydroxytetrahydro-2H-pyran-4-yl)methyl]piperidin-4-yl}methyl)-3-isopropyl-2-oxo-2,3-dihydro-1H-benzimidazole-1-carboxamide Hydrochloride The title compound was prepared according to the procedure described in Step 4 of Example 1 from 6-fluoro-N-({1-[(4-hydroxytetrahydro-2H-pyran-4-yl)methyl]piperidin-4-yl}methyl)-3-isopropyl-2-oxo-2,3-dihydro-1H-benzimidazole-1-carboxamide (step 1 of Example 8).

MS (ESI) m/z: 449 (M+H$^+$).

$^1$H-NMR (DMSO-d$_6$) δ: 1.46 (6H, d, J=6.9 Hz), 1.55-1.65 (4H, m), 1.70-1.91 (4H, m), 2.90-3.28 (8H, m), 3.50-3.67 (6H, m), 4.56-4.69 (1H, m), 5.30-5.37 (1H, m), 5.76 (1H, s), 7.08 (1H, td, J=9.0, 2.4 Hz), 7.44-7.49 (1H, m), 7.85 (1H, dd, J=9.5, 2.5 Hz), 8.81-8.85 (1H, m).

Anal. Calcd. for C$_{23}$H$_{34}$FN$_4$O$_4$Cl: C, 56.96; H, 7.07; N, 11.55. Found: C, 57.00; H, 7.20; N, 11.43.

PXRD pattern angle (2-Theta°): 10.0, 14.6, 16.2, 18.5, 23.2, 25.3, 27.3.

Example 9

5-fluoro-N-({1-[(4-hydroxytetrahydro-2H-pyran-4-yl)methyl]piperidin-4-yl}methyl)-3-isopropyl-2-oxo-2,3-dihydro-1H-benzimidazole-1-carboxamide

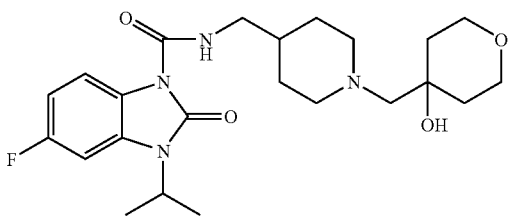

Step 1. (5-fluoro-2-nitrophenyl)isopropylamine

To a stirred mixture of 2,4-difluoro-1-nitrobenzene (4.77 g, 30 mmol) and K2CO3 (4.14 g, 30 mmol) in THF (30 mL) was added isopropyl amine (1.77 g, 30 mmol) in THF (10 mL) at 0° C. After being stirred for 13 h, the insoluble materials were removed by pad of Celite and the filtrate was consentrated under reduced pressure to give title compound (5.25 g, 88%) as a pale yellow oil.

MS (ESI) m/z: 405 (M+H$^+$).

$^1$H NMR (CDCl$_3$): δ 8.21 (1H, dd, J=9.3, 6.0 Hz), 6.48 (1H, dd, J=11.7, 2.6 Hz), 6.39-6.29 (1H, m), 3.81-3.66 (1H, m), 1.33 (6H, d, J=6.4 Hz)

Step 2. 6-fluoro-1-isopropyl-1,3-dihydro-2H-benzimidazol-2-one

A mixture of (5-fluoro-2-nitrophenyl)isopropylamine (Step 1 of Example 9, 5.85 g, 30 mmol) and 10% Pd—C (600 mg) in MeOH was stirred under atmosphere of hydrogen gas at room temperature for 12 h. The catalyst was filtered off on a pad of Celite, and the filtrate was evaporated under reduced pressure. To the residue was added 1,1'-carbonyldiimidazole (4.5 g, 28 mmol) and THF (100 μL) and then stirred at 100° C. for 10 h. After cooling, the volatile materials were removed under reduced pressure and the residue was partitioned between ethylacetate and H$_2$O. After extraction with ethylacetate (3 times), the combined organic phase was washed with brine, dried over MgSO$_4$ and concentrated. The residue was chromatographed on a column of silica gel eluting with hexane/ethyl acetate (2:1) to give 3.47 g (60%) of the title compound as a white solid.

MS (ESI) m/z: 195 (M+H$^+$), 193 (M−H$^+$).

$^1$H NMR (CDCl$_3$): δ 7.06-6.99 (1H, m), 6.90 (1H, dd, J=9.2, 2.4 Hz), 6.82-6.72 (1H, m), 4.83-4.62 (1H, m), 1.54 (6H, d, J=7.1 Hz)

Step 3. 5-fluoro-N-({1-[(4-hydroxytetrahydro-2H-pyran-4-yl)methyl]piperidin-4-yl}methyl)-3-isopropyl-2-oxo-2,3-dihydro-1H-benzimidazole-1-carboxamide To a stirred mixture of 6-fluoro-1-isopropyl-1,3-dihydro-2H-benzimidazol-2-one (Step 2 of Example 9, 0.58 g, 3 mmol) and p-nitrophenylchloroformate (0.66 g, 3.3 mmol) in dichloromethane (15 mL) was added triethylamine (1.25 mL, 9.0 mmol) at room temperature. After being stirred for 2 h, a solution of 4-{[4-(aminomethyl)piperidin-1-yl]methyl}tetrahydro-2H-pyran-4-ol (Step 2 of Example 1, 0.75 g, 3.3 mmol) in dichloromethane (15 mL) was added to the mixture. After being stirred for 4 h, the mixture was diluted with ethyl acetate (100 mL). Then, the organic layer was washed with 0.5 N NaOH aq. (10 mL) for 5 times and brine, dried over MgSO$_4$ and concentrated. The residue was chromatographed on a column of aminopropyl-silica gel eluting with hexane/ethyl acetate (3:1) to give 0.97 g (79%) of the title compound as a white solid.

MS (ESI) m/z: 449 (M+H$^+$).

$^1$H NMR (CDCl$_3$): δ 8.84-8.74 (1H, m), 8.21-8.11 (2H, m), 7.02-6.91 (2H, m), 4.68-4.56 (1H, m), 3.87-3.72 (4H, m), 3.34-3.25 (2H, m), 2.93-2.82 (2H, m), 2.42-2.25 (4H, m), 1.79-1.68 (2H, m), 1.67-1.29 (13H, m).

Anal. calcd. for C$_{23}$H$_{33}$N$_4$O$_4$F: C, 61.59; H, 7.42; N, 12.49. Found: C, 61.45; H, 7.33; N, 12.40.

Example 10

5,6-difluoro-N-({1-[(4-hydroxytetrahydro-2H-pyran-4-yl)methyl]piperidin-4-yl}methyl)-3-isopropyl-2-oxo-2,3-dihydro-1H-benzimidazole-1-carboxamide Hydrochloride

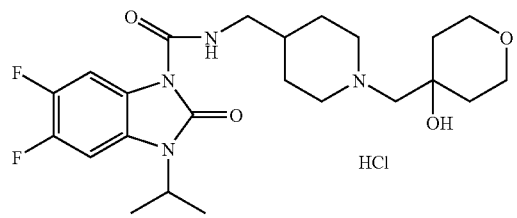

Step 1. 4,5-difluoro-N-isopropyl-2-nitroaniline 4,5-difluoro-2-nitroaniline (3.48 g, 20 mmol), 2,2-dimethoxypropane (11.9 mL, 100 mmol), and trifluoroacetic acid (1.6 mL, 21 mmol) were dissolved in toluene (40 mL) and stirred at room temperature for 1 h. A boron-pyridine complex (2.12 mL, 21 mmol) was slowly added. The reaction mixture was stirred for 20 h. The solvent was evaporated in vacuo, and the residue was taken up into water and extracted with dichloromethane. The organic extract was dried (Na$_2$SO$_4$) and concentrated in vacuo. The residue was chromatographed on a column of aminopropyl-silica gel eluting with hexane/ethyl acetate (30:1) to give 2.42 g (56%) of the title compound as a bright orange solid.

$^1$H NMR (CDCl$_3$): δ 8.05 (1H, dd, J=10.8, 8.6 Hz), 6.61 (1H, dd, J=12.6, 6.8 Hz), 3.77-3.62 (1H, m), 1.33 (6H, d, J=6.2 Hz).

Step 2. 5,6-difluoro-1-isopropyl-1,3-dihydro-2H-benzimidazol-2-one

The title compound was prepared according to the procedure described in Step 2 of Example 9 from 4,5-difluoro-N-isopropyl-2-nitroaniline (Step 1 of Example 10).

MS (ESI) m/z: 213 (M+H$^+$), 211 (M+H$^+$).

$^1$H NMR (CDCl$_3$): δ 7.00-6.89 (2H, m), 4.76-4.57 (1H, m), 3.86-3.69 (4H, m), 3.31 (2H, t, J=7.0 Hz), 2.95-2.82 (2H, m), 2.35 (2H, t, J=, 13.7 Hz), 2.31 (2H, s), 1.67-1.25 (10H, m), 1.55 (6H, d, J=7.7 Hz).

Step 3. 5,6-difluoro-N-({1-[(4-hydroxytetrahydro-2H-pyran-4-yl)methyl]piperidin-4-yl}methyl)-3-isopropyl-2-oxo-2,3-dihydro-1H-benzimidazole-1-carboxamide The title compound was prepared according to the procedure described in Step 3 of Example 9 from 5,6-difluoro-1-isopropyl-1,3-dihydro-2H-benzimidazol-2-one (Step 2 of Example 10) and 4-{[4-(aminomethyl)piperidin-1-yl]methyl}tetrahydro-2H-pyran-4-ol (Step 2 of Example 1).

MS (ESI) m/z: 467 (M+H$^+$).
$^1$H NMR (CDCl$_3$): δ 8.88-8.78 (1H, m), 8.25-8.15 (1H, m), 6.94-6.79 (2H, m), 4.73-4.57 (1H, m), 3.86-3.69 (4H, m), 3.31 (2H, t, J=7.0 Hz), 2.95-2.82 (2H, m), 2.35 (2H, t, J=, 13.7 Hz), 2.31 (2H, s), 1.67-1.25 (10H, m), 1.55 (6H, d, J=7.7 Hz).

Step 4. 5,6-difluoro-N-({1-[(4-hydroxytetrahydro-2H-pyran-4-yl)methyl]piperidin-4-yl}methyl)-3-isopropyl-2-oxo-2,3-dihydro-1H-benzimidazole-1-carboxamide Hydrochloride A mixture of 5,6-difluoro-N-({1-[(4-hydroxytetrahydro-2H-pyran-4-yl)methyl]piperidin-4-yl}methyl)-3-isopropyl-2-oxo-2,3-dihydro-1H-benzimidazole-1-carboxamide (Step 3 of Example 10, 113 mg, 0.242 mmol) and 10% HCl-methanol (5 mL) was stirred for 1 h. Then, the volatile components were removed under reduced pressure and the residue was recrystallized from ethanol-diethyl ether to give 88 mg (72%) of the title compound as a colorless powder.

MS (ESI) m/z: 467 (M+H$^+$).
$^1$H NMR (DMSO-d$_6$): δ 8.82-8.71 (1H, m), 8.08-7.93 (1H, m), 7.78-7.67 (1H, m), 5.35-5.26 (1H, m), 4.69-4.52 (1H, m), 3.70-3.51 (6H, m), 3.41-2.91 (7H, m), 1.94-1.53 (8H, m), 1.45 (6H, d, J=7.0 Hz).
Anal. calcd. for C$_{23}$H$_{33}$N$_4$O$_4$F$_2$Cl.1H$_2$O: C, 53.96; H, 6.69; N, 10.94. Found: C, 53.67; H, 6.64; N, 10.89.

Example 11

6-chloro-N-({1-[(4-hydroxytetrahydro-2H-pyran-4-yl)methyl]piperidin-4-yl}methyl)-3-isopropyl-2-oxo-2,3-dihydro-1H-benzimidazole-1-carboxamide Hydrochloride

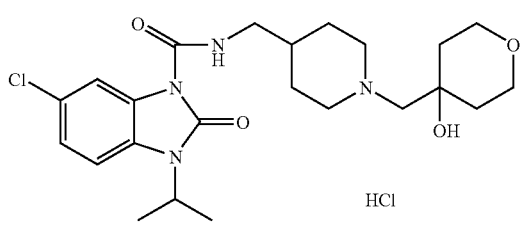

Step 1. 6-chloro-N-({1-[(4-hydroxytetrahydro-2H-pyran-4-yl)methyl]piperidin-4-yl}methyl)-3-isopropyl-2-oxo-2,3-dihydro-1H-benzimidazole-1-carboxamide The title compound was prepared according to the procedure described in Step 3 of Example 9 from 5-chloro-1-isopropyl-1,3-dihydro-2H-benzimidazol-2-one (I. Tapia et al., *J. Med. Chem.*, 42, 2880 (1999)) and 4-{[4-(aminomethyl)piperidin-1-yl]methyl}tetrahydro-2H-pyran-4-ol (Step 2 of Example 1).

MS (ESI) m/z: 465 (M+H$^+$).
$^1$H NMR (CDCl$_3$): δ 8.33-8.30 (1H, m), 7.19-7.14 (1H, m), 7.04-7.03 (1H, m), 4.73-4.57 (1H, m), 3.82-3.71 (4H, m), 3.31 (2H, t, J=6.4 Hz), 2.95-2.83 (2H, m), 2.41-2.29 (4H, m), 1.79-1.68 (2H, m), 1.67-1.25 (8H, m), 1.54 (6H, d, J=7.0 Hz).

Step 2. 6-chloro-N-({1-[(4-hydroxytetrahydro-2H-pyran-4-yl)methyl]piperidin-4-yl}methyl)-3-isopropyl-2-oxo-2,3-dihydro-1H-benzimidazole-1-carboxamide hydrochloride The title compound was prepared according to the procedure described in Step 4 of Example 10 from 6-chloro-N-({1-[(4-hydroxytetrahydro-2H-pyran-4-yl)methyl]piperidin-4-yl}methyl)-3-isopropyl-2-oxo-2,3-dihydro-1H-benzimidazole-1-carboxamide (Step 1 of Example 11).

MS (ESI) m/z: 465 (M+H$^+$).
$^1$H NMR (DMSO-d$_6$): δ 8.84-8.76 (1H, m), 8.10-8.07 (1H, m), 7.51-7.45 (1H, m), 7.32-7.25 (1H, m), 5.38-5.32 (1H, m), 4.73-4.56 (1H, m), 3.70-3.55 (6H, m), 3.41-2.91 (7H, m), 1.95-1.58 (8H, m), 1.48 (6H, d, J=7.7 Hz).
Anal. calcd. for C$_{23}$H$_{34}$N$_4$O$_4$Cl$_2$~0.5H$_2$O: C, 54.12; H, 6.91; N, 10.98. Found: C, 53.85; H, 6.90; N, 10.78.

Example 12

5-chloro-N-({1-[(4-hydroxytetrahydro-2H-pyran-4-yl)methyl]piperidin-4-yl}methyl)-3-isopropyl-2-oxo-2,3-dihydro-1H-benzimidazole-1-carboxamide

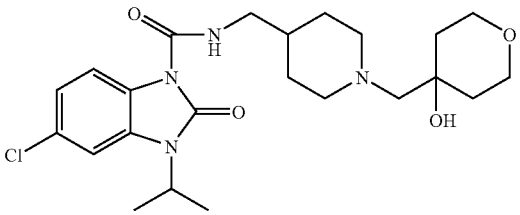

Step 1. 5-chloro-N-isopropyl-2-nitroaniline

The title compound was prepared according to the procedure described in Step 1 of Example 10 from 5-chloro-2-nitroaniline.

$^1$H NMR (CDCl$_3$): δ 8.12 (1H, d, J=9.2 Hz), 6.84 (1H, d, J=2.0 Hz), 6.57 (1H, dd, J=9.2, 2.0 Hz), 3.81-3.71 (1H, m), 1.33 (6H, d, J=6.2 Hz)

Step 2. 6-chloro-1-isopropyl-1,3-dihydro-2H-benzimidazol-2-one

A mixture of 5-chloro-N-isopropyl-2-nitroaniline (Step 1 of Example 12, 0.76 g, 3.54 mmol), iron (0.99 g, 17.7 mmol) and ammonium chloride (0.38 g, 7.08 mmol) was suspended in ethanol (27 mL) and H$_2$O (9 mL). Then, the mixture was heated at 80° C. for 3 h. After cooling, the insoluble materials was filtered off on a pad of Celite, and the filtrate was evaporated under reduced pressure. To the residue was added N,N'-carbonyldiimidazole (CDI, 0.57 g, 3.50 mmol) and THF (10 mL) and then stirred at 100° C. for 10 h. After cooling, the volatile materials were removed under reduced pressure and the residue was partitioned between ethylacetate and H$_2$O. After extraction with ethylacetate (3 times), the combined organic phase was washed with brine, dried over MgSO$_4$ and concentrated. The residue was chromatographed on a column of silica gel eluting with hexane/ethyl acetate (2:1) to give 0.30 g (40%) of the title compound as a white solid.

$^1$H NMR (CDCl$_3$): δ 6.99-6.90 (2H, m), 6.84-6.74 (1H, m), 4.94-4.77 (1H, m), 1.64 (6H, d, J=7.0 Hz)

Step 3. 5-chloro-N-({1-[(4-hydroxytetrahydro-2H-pyran-4-yl)methyl]piperidin-4-yl}methyl)-3-isopropyl-2-oxo-2,3-dihydro-1H-benzimidazole-1-carboxamide The title compound was prepared according to the procedure described in Step 3 of Example 9 from 6-chloro-1-isopropyl-1,3-dihydro-2H-benzimidazol-2-one (Step 2 of Example 12) and 4-{[4-(aminomethyl)piperidin-1-yl]methyl}tetrahydro-2H-pyran-4-ol (Step 2 of Example 1).

MS (ESI) m/z: 465 (M+H$^+$).

$^1$H NMR (CDCl$_3$): δ 8.88-8.78 (1H, m), 8.21-8.14 (1H, m), 7.19-7.10 (2H, m), 4.73-4.56 (1H, m), 3.87-3.69 (4H, m), 3.30 (2H, t, J=6.2 Hz), 2.94-2.84 (2H, m), 2.41-2.27 (4H, m), 1.79-1.68 (2H, m), 1.67-1.25 (11H, m).

Anal. calcd. for C$_{23}$H$_{33}$N$_4$O$_4$Cl: C, 59.41; H, 7.15; N, 12.05. Found: C, 59.27; H, 7.10; N, 11.72.

Example 13

N-({1-[(4-hydroxytetrahydro-2H-pyran-4-yl)methyl]piperidin-4-yl}methyl)-3-isopropyl-5-methyl-2-oxo-2,3-dihydro-1H-benzimidazole-1-carboxamide

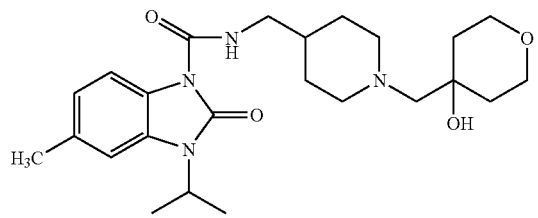

Step 1. N-isopropyl-5-methyl-2-nitroaniline

The title compound was prepared according to the procedure described in Step 1 of Example 9 from 2-fluoro-4-methyl-1-nitrobenzene.

$^1$H NMR (CDCl$_3$): δ 8.12-8.01 (2H, m), 6.63 (1H, brs), 6.42 (1H, d, J=10.3 Hz), 3.94-3.72 (1H, m), 2.33 (3H, s), 1.32 (6H, d, J=6.4 Hz)

Step 2. 1-isopropyl-6-methyl-1,3-dihydro-2H-benzimidazol-2-one

The title compound was prepared according to the procedure described in Step 2 of Example 9 from N-isopropyl-5-methyl-2-nitroaniline (Step 1 of Example 13).

MS (ESI) m/z: 191 (M+H$^+$).

$^1$H NMR (CDCl$_3$): δ 7.04-6.93 (2H, m), 6.90-6.80 (1H, m), 4.82-4.63 (1H, m), 2.40 (3H, s), 1.55 (6H, d, J=7.0 Hz).

Step 3. N-({1-[(4-hydroxytetrahydro-2H-pyran-4-yl)methyl]piperidin-4-yl}methyl)-3-isopropyl-5-methyl-2-oxo-2,3-dihydro-1H-benzimidazole-1-carboxamide The title compound was prepared according to the procedure described in Step 3 of Example 9 from 1-isopropyl-6-methyl-1,3-dihydro-2H-benzimidazol-2-one (Step 2 of Example 13) and 4-{[4-(aminomethyl)piperidin-1-yl]methyl}tetrahydro-2H-pyran-4-ol (Step 2 of Example 1).

MS (ESI) m/z: 445 (M+H$^+$).

$^1$H NMR (CDCl$_3$): δ 8.97-8.84 (1H, m), 8.10 (1H, d, J=8.8 Hz), 7.01-6.93 (2H, m), 4.76-4.58 (1H, m), 3.85-3.69 (4H, m), 3.30 (2H, t, J=6.4 Hz), 2.94-2.82 (2H, m), 2.41 (3H, s), 2.43-2.27 (4H, m), 1.80-1.68 (2H, m), 1.67-1.25 (11H, m).

Anal. calcd. for C$_{24}$H$_{36}$N$_4$O$_4$: C, 64.84; H, 8.16; N, 12.60. Found: C, 64.78; H, 8.29; N, 12.58.

Example 14

N-({1-[(4-hydroxytetrahydro-2H-pyran-4-yl)methyl]piperidin-4-yl}methyl)-3-isopropyl-4-methyl-2-oxo-2,3-dihydro-1H-benzimidazole-1-carboxamide

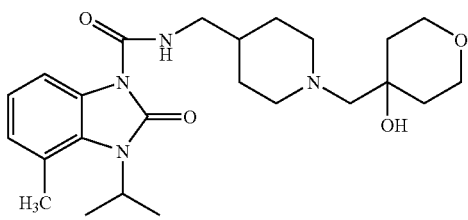

Step 1. N-({1-[(4-hydroxytetrahydro-2H-pyran-4-yl)methyl]piperidin-4-yl}methyl)-3-isopropyl-4-methyl-2-oxo-2,3-dihydro-1H-benzimidazole-1-carboxamide The title compound was prepared according to the procedure described in Step 3 of Example 9 from 1-isopropyl-7-methyl-1,3-dihydro-2H-benzimidazol-2-one (I. Tapia et al., J. Med. Chem., 42, 2880 (1999)) and 4-{[4-(aminomethyl)piperidin-1-yl]methyl}tetrahydro-2H-pyran-4-ol (Step 2 of Example 1).

MS (ESI) m/z: 445 (M+H$^+$).

$^1$H NMR (CDCl$_3$): δ9.11-8.97 (1H, m), 8.17 (1H, d, J=7.7 Hz), 7.10-6.88 (2H, m), 4.99-4.82 (1H, m), 3.91-3.69 (4H, m), 3.29 (2H, t, J=6.2 Hz), 2.94-2.82 (2H, m), 2.59 (3H, s), 2.43-2.27 (4H, m), 1.84-1.19 (7H, m), 1.62 (6H, d, J=6.8 Hz).

Anal. calcd. for C$_{24}$H$_{36}$N$_4$O$_4$: C, 64.84; H, 8.16; N, 12.60. Found: C, 64.73; H, 8.35; N, 12.56.

Example 15

N-({1-[(4-hydroxytetrahydro-2H-pyran-4-yl)methyl]piperidin-4-yl}methyl)-3-isopropyl-4,5-dimethyl-2-oxo-2,3-dihydro-1H-benzimidazole-1-carboxamide Hydrochloride

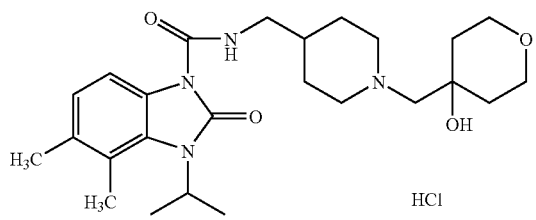

Step 1. N-isopropyl-2,3-dimethyl-6-nitroaniline

The title compound was prepared according to the procedure described in Step 1 of Example 10 from 2,3-dimethyl-6-nitroaniline.

$^1$H NMR (CDCl$_3$): δ 7.82 (1H, d, J=8.6 Hz), 6.79 (1H, d, J=8.4 Hz), 3.52-3.34 (1H, m), 2.30 (3H, s), 2.24 (3H, s), 1.11 (6H, d, J=6.2 Hz)

Step 2. 1-isopropyl-6,7-dimethyl-1,3-dihydro-2H-benzimidazol-2-one

The title compound was prepared according to the procedure described in Step 2 of Example 9 from N-isopropyl-2,3-dimethyl-6-nitroaniline (Step 1 of Example 15).

$^1$H NMR (CDCl$_3$): δ 7.11 (1H, brs), 6.92-6.70 (1H, m), 5.00-4.82 (1H, m), 2.45 (3H, s), 2.32 (3H, s), 1.63 (6H, d, J=7.0 Hz).

Step 3. N-({1-[(4-hydroxytetrahydro-2H-pyran-4-yl)methyl]piperidin-4-yl}methyl)-3-isopropyl-4,5-dimethyl-2-oxo-2,3-dihydro-1H-benzimidazole-1-carboxamide Hydrochloride To a stirred mixture of 1-isopropyl-6,7-dimethyl-1,3-dihydro-2H-benzimidazol-2-one (Step 2 of Example 15, 204 mg, 1 mmol) and p-nitrophenylchloroformate (220 mg, 1.1 mmol) in dichloromethane (7 mL) was added triethylamine (0.42 mL, 3.0 mmol) at room temperature. After being stirred for 2 h, a solution of 4-{[4-(aminomethyl)piperidin-1-yl]methyl}tetrahydro-2H-pyran-4-ol (Step 2 of Example 1, 230 mg, 1.0 mmol) in dichloromethane (3 mL) was added to the mixture. After being stirred for 4 h, the mixture was diluted with ethyl acetate (50 mL). Then, the organic layer was washed with 0.5 N NaOH aq. (5 mL) for 5 times and brine, dried over MgSO$_4$ and concentrated. The residue was filtered through pad of aminopropyl-silica gel eluting with hexane/ethyl acetate (3:1) and the filtrate was concentrated. To the mixture was added 10% HCl-methanol (5 mL) was stirred for 1 h. Then, the volatile components were removed under reduced pressure and the residue was recrystallized from ethanol-diethyl ether to give 100 mg (20%) of the title compound as a colorless powder.

MS (ESI) m/z: 459 (M+H$^+$).

$^1$H NMR (DMSO-d$_6$): δ 8.96-8.87 (1H, m), 7.84 (1H, d, J=8.3 Hz), 6.95 (1H, d, J=8.3 Hz), 5.34-5.21 (1H, m), 5.01-4.86 (1H, m), 3.69-3.53 (6H, m), 3.41-2.91 (7H, m), 2.45 (3H, s), 2.28 (3H, s), 1.87-1.70 (3H, m), 1.67-1.48 (5H, m), 1.52 (6H, d, J=6.6 Hz).

Anal. calcd. for C$_{25}$H$_{39}$N$_4$O$_4$Cl.0.5H$_2$O: C, 59.57; H, 8.00; N, 11.12. Found: C, 59.53; H, 7.98; N, 11.10.

Example 16

6-fluoro-N-({1-[(4-hydroxytetrahydro-2H-pyran-4-yl)methyl]piperidin-4-yl}methyl)-3-isopropyl-5-methyl-2-oxo-2,3-dihydro-1H-benzimidazole-1-carboxamide Hydrochloride

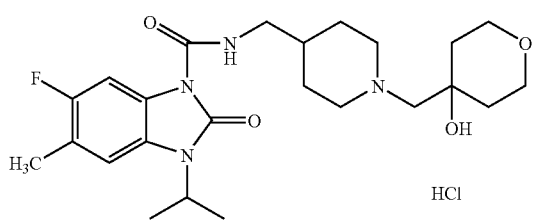

Step 1. 4-fluoro-N-isopropyl-5-methyl-2-nitroaniline

The title compound was prepared according to the procedure described in Step 1 of Example 9 from 1,4-difluoro-2-methyl-5-nitrobenzene (T. Timothy et al., *J. Med. Chem.*, 35, 2321 (1992)).

MS (ESI) m/z: 213 (M+H$^+$).

$^1$H NMR (CDCl$_3$): δ 7.82 (1H, d, J=10.3 Hz), 6.64 (1H, d, J=6.4 Hz), 3.88-3.67 (1H, m), 2.30 (3H, s), 1.31 (6H, d, J=6.4 Hz)

Step 2. 5-fluoro-1-isopropyl-6-methyl-1,3-dihydro-2H-benzimidazol-2-one

The title compound was prepared according to the procedure described in Step 2 of Example 9 from 4-fluoro-N-isopropyl-5-methyl-2-nitroaniline (Step 1 of Example 16).

MS (ESI) m/z: 209 (M+H$^+$).

$^1$H NMR (CDCl$_3$): δ 7.00-6.96 (1H, m), 6.92-6.90 (1H, m), 4.75-4.56 (1H, m), 2.31 (3H, s), 1.55 (6H, d, J=7.0 Hz).

Step 3. 6-fluoro-N-({1-[(4-hydroxytetrahydro-2H-pyran-4-yl)methyl]piperidin-4-yl}methyl)-3-isopropyl-5-methyl-2-oxo-2,3-dihydro-1H-benzimidazole-1-carboxamide The title compound was prepared according to the procedure described in Step 3 of Example 9 from 5-fluoro-1-isopropyl-6-methyl-1,3-dihydro-2H-benzimidazol-2-one (Step 2 of Example 16) and 4-{[4-(aminomethyl)piperidin-1-yl]methyl}tetrahydro-2H-pyran-4-ol (Step 2 of Example 1).

MS (ESI) m/z: 463 (M+H$^+$).

$^1$H NMR (CDCl$_3$): δ 8.92-8.83 (1H, m), 7.96 (1H, d, J=10.1 Hz), 6.91 (1H, d, J=6.2 Hz), 4.75-4.56 (1H, m), 3.85-3.70 (4H, m), 3.30 (2H, t, J=6.4 Hz), 2.94-2.82 (2H, m), 2.42-2.29 (7H, m), 1.84-1.19 (7H, m), 1.55 (6H, d, J=7.0 Hz).

Step 4. 6-fluoro-N-({1-[(4-hydroxytetrahydro-2H-pyran-4-yl)methyl]piperidin-4-yl}methyl)-3-isopropyl-5-methyl-2-oxo-2,3-dihydro-1H-benzimidazole-1-carboxamide hydrochloride The title compound was prepared according to the procedure described in Step 4 of Example 10 from 6-fluoro-N-({1-[(4-hydroxytetrahydro-2H-pyran-4-yl)methyl]piperidin-4-yl}methyl)-3-isopropyl-5-methyl-2-oxo-2,3-dihydro-1H-benzimidazole-1-carboxamide (Step 3 of Example 16).

MS (ESI) m/z: 463 (M+H$^+$).

$^1$H NMR (DMSO-d$_6$): 89.55-9.11 (1H, m), 8.89-8.74 (1H, m), 7.77 (1H, d, J=10.4 Hz), 7.40 (1H, d, J=6.6 Hz), 5.42-5.34 (1H, m), 4.70-4.56 (1H, m), 3.69-3.53 (6H, m), 3.52-2.91 (7H, m), 2.29 (3H, s), 1.87-1.70 (3H, m), 1.95-1.55 (8H, m), 1.48 (6H, d, J=6.8 Hz).

Anal. calcd. for C$_{24}$H$_{36}$N$_4$O$_4$FCl: C, 57.76; H, 7.27; N, 11.23. Found: C, 57.47; H, 7.40; N, 11.05.

Preparation 1

Step 1. tert-Butyl 4-({[(3-isopropyl-2-oxo-2,3-dihydro-1H-benzimidazol-1-yl)carbonyl]amino}methyl)piperidine-1-carboxylate

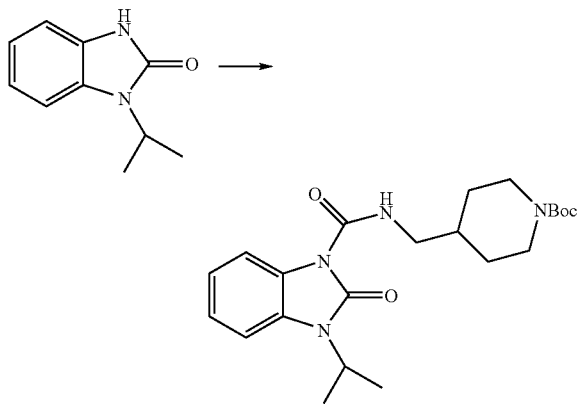

To a stirred solution of 1-isopropyl-1,3-dihydro-2H-benzimidazol-2one (*J. Med. Chem.* 1999, 42, 2870-2880) (3.00 g, 17.02 mmol) and triethylamine (7.12 ml, 51.06 mmol) in 70 ml tetrahydrofuran was added triphosgen (5.15 g, 17.02 mmol) in 14 ml tetrahydrofuran at room temperature. The reaction mixture was refluxed for 19 hours. The mixture was then cooled to room temperature, tert-butyl 4-(aminomethyl)piperidine-1-carboxylate (J. Prugh, L. A. Birchenough and M. S. Egbertson, *Synth. Commun.,* 1992, 22, 2357-60) (3.28 g, 15.32 mmol) in 10 ml tetrahydrofuran was added. The reaction mixture was refluxed for another 24 hours. Then cooled and basified with aqueous saturated NaHCO$_3$ 50 ml, and extracted with ethyl acetate 100 ml for three times. The combined extract was washed with brine, dried over MgSO$_4$ and concentrated. Flash chromatography of the residue (elutent: hexane/ethyl acetate=5/1 to 1/2) afforded a colorless oil 3.99 g (62%) as the titled compound.

$^1$H-NMR (CDCl$_3$) δ: 9.04-8.88 (1H, m), 8.83-8.20 (1H, m), 7.26-7.10 (3H, m), 4.80-4.60 (1H, m), 4.28-4.02 (2H, m), 3.32 (2H, t, J=6.1 Hz), 2.82-2.60 (2H, m), 1.94-1.10 (5H, m), 1.57 (6H, d, J=7.1 Hz), 1.45 (9H, s).

Step 2. 3-Isopropyl-2-oxo-N-(piperidin-4-ylmethyl)-2,3-dihydro-1H-benzimidazole-1-carboxamide

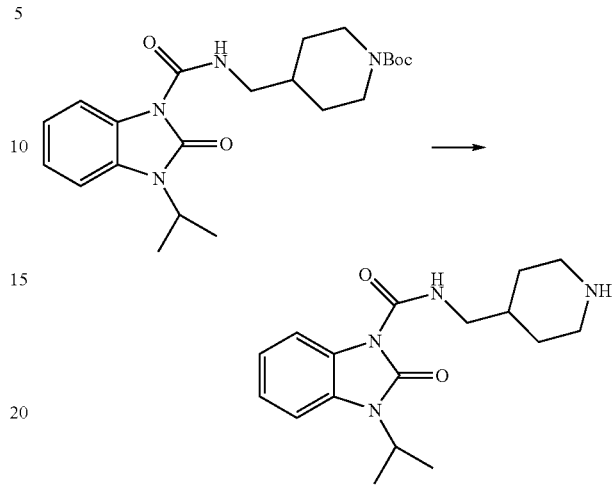

A solution of tert-butyl 4-({[(3-isopropyl-2-oxo-2,3-dihydro-1H-benzimidazol-1-yl)carbonyl]amino}methyl)piperidine-1-carboxylate (3.992 g, 9.58 mmol) in 50 ml 10% hydrochloric acid in methanol and 10 ml concentrated hydrochloric acid was stirred at room temperature for 18 hours. The mixture was then concentrated and basified with aqueous Na$_2$CO$_3$, extracted with CHCl$_3$ 100 ml for 3 times. The combined extract was dried and concentrated. Flash chromatography of the residue (NH-silica gel, elutent: CH$_2$Cl$_2$/methanol=100/1) afforded a colorless oil 2.272 g (75%) as the titled compound.

MS (ESI) m/z: 317 (M+H)$^+$.

$^1$H-NMR (CDCl$_3$) δ: 8.93 (1H, br), 8.32-8.22 (1H, m), 7.24-7.02 (3H, m), 4.80-4.61 (1H, m), 3.31 (2H, t, J=6.0 Hz), 3.20-3.05 (2H, m), 2.79-2.54 (2H, m), 1.84-1.52 (3H, m), 1.57 (6H, d, J=6.9 Hz), 1.36-1.13 (2H, m).

Step 3. N-{[1-(3-Hydroxy-3-methyl-2-oxobutyl)piperidin-4-yl]methyl}-3-isopropyl-2-oxo-2,3-dihydro-1H-benzimidazole-1-carboxamide, Monooxalate Salt

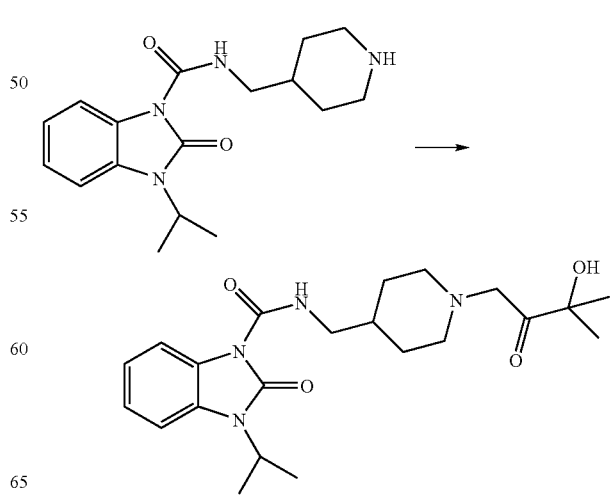

A mixture of 3-isopropyl-2-oxo-N-(piperidin-4-ylmethyl)-2,3-dihydro-1H-benzimidazole-1-carboxamide (250 mg, 0.790 mmol), 1-bromo-3-hydroxy-3-methylbutan-2-one (G. Bertram; A. Scherer; W. Steglich; W. Weber, *Tetrahedron Lett.*, 1996, 37, 7955-7958) (181 mg, 1.343 mmol) and triethylamine (0.28 ml, 1.975 mmol) in 8 ml tetrahydrofuran was refluxed for 15 hours. Then cooled and diluted with 100 ml ethyl acetate and was washed with aqueous $NaHCO_3$ 20 ml, brine, dried over $MgSO_4$ and concentrated. Flash chromatography of the residue (elutent: $CH_2Cl_2$/methanol=100/1 to 30/1) afforded a colorless oil 202 mg (61%). The oil (202 mg) was dissolved in 3 ml methanol and acidified with a solution of 44 mg oxalic acid in 1 ml MeOH. The mixture was concentrated. Recrystallization of the resulting solid with EtOH—AcOEt afforded a white solid 246 mg as the titled compound.

MS (ESI) m/z: 417 (M+H)$^+$.

m.p.: 140.5° C.

IR (KBr) ν: 3404, 3306, 2980, 2941, 1728, 1690, 1612, 1541 cm$^{-1}$.

$^1$H-NMR (CDCl$_3$) (free base) δ: 8.90 (1H, br) 8.30-8.20 (1H, m), 7.24-7.10 (3H, m), 4.78-4.61 (1H, m), 3.37 (2H, s), 3.33 (2H, t, J=6.3 Hz), 3.00-2.86 (2H, m), 2.22-2.06 (2H, m), 1.90-1.22 (5H, m), 1.57 (6H, d, J=7.0 Hz), 1.35 (6H, s).

$^1$H-NMR (DMSO-d$_6$) (salt form) δ: 8.92-8.81 (1H, m) 8.07 (1H, dd, J=7.7, 6.8 Hz), 7.44 (1H, d, J=7.7 Hz), 7.28-7.10 (2H, m), 4.74-4.60 (1H, m), 4.36 (2H, by), 4.00-2.70 (6H, m), 1.90-1.44 (5H, m), 1.49 (6H, d, J=6.4 Hz), 1.24 (6H, s).

Anal. Calcd. for $C_{24}H_{34}N_4O_8 \cdot 0.3C_2H_6O \cdot 1H_2O$: C, 54.88; H, 7.08; N, 10.41. Found: C, 55.26; H, 7.18; N, 10.07.

All publications, including but not limited to, issued patents, patent applications, and journal articles, cited in this application are each herein incorporated by reference in their entirety.

Although the invention has been described above with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

The invention claimed is:

1. A compound of the formula (I):

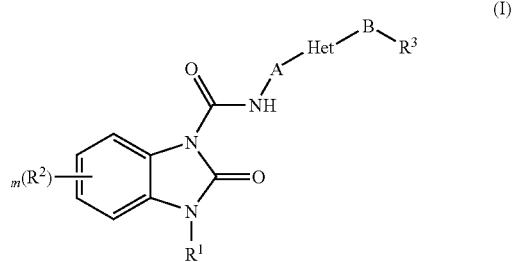

wherein:

Het represents

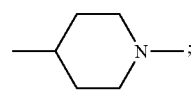

A represents a methylene group;

B represents a covalent bond or an alkylene group having from 1 to 5 carbon atoms, wherein when $R^3$ represents a heterocyclic group said alkylene group is optionally substituted by an oxo group;

$R^1$ represents an isopropyl group or a cyclopentyl group;

each $R^2$ independently represents a halogen atom or an alkyl group having from 1 to 4 carbon atoms; m is 0, 1, 2, 3, or 4;

$R^3$ represents (i) a cycloalkyl group having from 3 to 8 carbon atoms, said cycloalkyl group being substituted by 1 to 5 substituents independently selected from the group consisting of substituents α$^2$, or (ii) a heterocyclic group having from 3 to 8 atoms, said heterocyclic group being unsubstituted or substituted by 1 to 5 substituents independently selected from the group consisting of substituents β;

wherein said substituents α$^2$ are hydroxy, amino, hydroxy-substituted alkyl having from 1 to 4 carbon atoms, and alkoxy having from 1 to 4 carbon atoms; and wherein said substituents β are hydroxy, hydroxy-substituted alkyl having from 1 to 4 carbon atoms, amino, alkyl having from 1 to 4 carbon atoms, amino-substituted alkyl having from 1 to 4 carbon atoms, and carbamoyl;

or a pharmaceutically acceptable salt thereof.

2. The compound of claim 1, wherein:

B represents an alkylene group having from 1 to 4 carbon atoms, wherein when $R^3$ represents a heterocyclic group said alkylene group is optionally substituted by an oxo group; each $R^2$ independently represents a halogen atom or an alkyl group having from 1 to 2 carbon atoms; m is 0, 1 or 2; and $R^3$ represents (i) a cycloalkyl group having from 4 to 7 carbon atoms, said cycloalkyl group being substituted by 1 to 3 substituents independently selected from the group consisting of substituents α$^2$, or (ii) a heterocyclic group having from 4 to 7 atoms, said heterocyclic group being unsubstituted or substituted by 1 to 3 substituents independently selected from the group consisting of substituents β;

or a pharmaceutically acceptable salt thereof.

3. The compound of claim 1, wherein:

B represents an alkylene group having from 1 to 2 carbon atoms;

$R^1$ represents an isopropyl group;

each $R^2$ independently represents fluorine, chlorine, or methyl; and $R^3$ represents (i) a cycloalkyl group having from 5 to 7 carbon atoms, said cycloalkyl group being substituted by 1 to 2 substituents independently selected from the group consisting of substituents α$^2$, or (ii) a heterocyclic group having from 5 to 7 atoms, said heterocyclic group being unsubstituted or substituted by 1 to 2 substituents independently selected from the group consisting of substituents β;

wherein said substituents α$^2$ are hydroxy, amino, and alkoxy having from 1 to 2 carbon atoms; and wherein said substituents β are hydroxy, hydroxy-substituted alkyl having from 1 to 2 carbon atoms, amino, amino-substituted alkyl having from 1 to 2 carbon atoms, and carbamoyl;

or a pharmaceutically acceptable salt thereof.

4. The compound of claim 1, wherein:

B represents a methylene group;

$R^1$ represents an isopropyl group;

$R^2$ represents a fluorine atom; m is 0 or 1; and

R³ represents (i) a cycloalkyl group having from 5 to 6 carbon atoms, said cycloalkyl group being substituted by 1 to 2 substituents independently selected from hydroxy or amino, or (ii) a heterocyclic group having from 5 to 6 atoms, said heterocyclic group being unsubstituted or substituted by 1 to 2 substituents independently selected from hydroxy or amino;

or a pharmaceutically acceptable salt thereof.

5. The compound of claim 1, wherein:

B represents a methylene group;

R¹ represents an isopropyl group;

m is 0; and

R³ represents (i) a cyclohexyl group substituted by 1 to 2 substituents independently selected from hydroxy or amino, or (ii) a heterocyclic group having from 6 atoms, said heterocyclic group being substituted by a hydroxy or an amino;

or a pharmaceutically acceptable salt thereof.

6. The compound of claim 5, wherein R³ represents (i) a cyclohexyl group substituted by 1 or 2 hydroxy groups, or (ii) a tetrahydropyran group substituted by 1 or 2 hydroxy groups, or a pharmaceutically acceptable salt thereof.

7. The compound of claim 6, wherein R³ represents hydroxytetrahydropyranyl or dihydroxycyclohexyl, or a pharmaceutically acceptable salt thereof.

8. The compound of claim 1, which is selected from:

N-({1-[(4-hydroxytetrahydro-2H-pyran-4-yl)methyl]piperidin-4-yl}methyl)-3-isopropyl-2-oxo-2,3-dihydro-1H-benzimidazole-1-carboxamide;

N-({1-[(trans-1,4-dihydroxyhexyl)methyl]piperidin-4-yl}methyl)-3-isopropyl-2-oxo-2,3-dihydro-1H-benzimidazole-1-carboxamide;

N-({1-[(cis-1,4-dihydroxyhexyl)methyl]piperidin-4-yl}methyl)-3-isopropyl-2-oxo-2,3-dihydro-1H-benzimidazole-1-carboxamide; or 6-fluoro-N-({1-[(4-hydroxytetrahydro-2H-pyran-4-yl)methyl]piperidin-4-yl}methyl)-3-isopropyl-2-oxo-2,3-dihydro-1H-benzimidazole-1-carboxamide;

or a pharmaceutically acceptable salt thereof.

9. The compound of any one of claims 1 to 8, in the form of a hydrochloride or hemiedisylate salt.

10. A pharmaceutical composition comprising the compound of any one of claims 1 to 8 or a pharmaceutically acceptable salt thereof, together with at least one pharmaceutically acceptable excipient.

11. A compound of the formula (I):

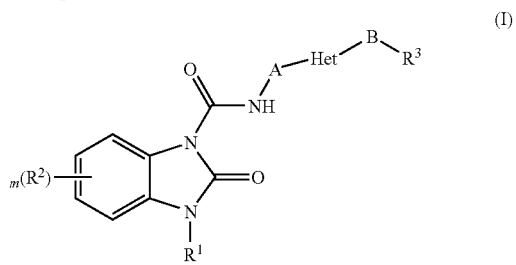

wherein:

Het represents

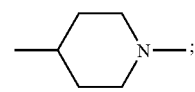

A represents a methylene group;

B represents a covalent bond or an alkylene group having from 1 to 5 carbon atoms, wherein when R3 represents a heterocyclic group said alkylene group is optionally substituted by an oxo group;

R¹ represents an isopropyl group or a cyclopentyl group;

each R² independently represents a halogen atom or an alkyl group having from 1 to 4 carbon atoms; m is 0, 1, 2, 3, or 4;

R³ represents (i) a cycloalkyl group having from 3 to 8 carbon atoms, said cycloalkyl group being substituted by 1 to 5 substituents independently selected from the group consisting of substituents α², or (ii) a heterocyclic group having from 3 to 8 atoms, said heterocyclic group being unsubstituted or substituted by 1 to 5 substituents independently selected from the group consisting of substituents β;

wherein said substituents α² are hydroxy, amino, hydroxy-substituted alkyl having from 1 to 4 carbon atoms, carboxyl-substituted alkyl having 1 to 4 carbon atoms, and alkoxy having from 1 to 4 carbon atoms; and wherein said substituents β are hydroxy, hydroxy-substituted alkyl having from 1 to 4 carbon atoms, carboxyl-substituted alkyl having 1 to 4 carbon atoms, amino, alkyl having from 1 to 4 carbon atoms, amino-substituted alkyl having from 1 to 4 carbon atoms, and carbamoyl;

or a pharmaceutically acceptable salt thereof.

12. A pharmaceutical composition comprising the compound of any one of claims 1 to 8 or a pharmaceutically acceptable salt thereof, and at least one other pharmacologically active agent.

* * * * *